US011672845B2

(12) United States Patent
Jan

(10) Patent No.: US 11,672,845 B2
(45) Date of Patent: Jun. 13, 2023

(54) COMPOSITION FOR PROMOTING LOCAL MUSCLE GROWTH OR SLOWING DOWN OR PREVENTING LOCAL MUSCLE ATROPHY AND USE THEREOF

(71) Applicants: Sulawan Charoenfuprasert, Hong Kong (CN); Soulyoung Biotech Co., Ltd., New Taipei (TW)

(72) Inventor: Hsun-Jin Jan, Taoyuan (CN)

(73) Assignee: SOULYOUNG BIOTECH CO., LTD., New Taipei (TW)

( * ) Notice: Subject to any disclaimer, the term of this patent is extended or adjusted under 35 U.S.C. 154(b) by 239 days.

(21) Appl. No.: 16/981,391

(22) PCT Filed: Mar. 21, 2018

(86) PCT No.: PCT/CN2018/079716

§ 371 (c)(1),
(2) Date: Sep. 16, 2020

(87) PCT Pub. No.: WO2019/178759

PCT Pub. Date: Sep. 26, 2019

(65) Prior Publication Data

US 2021/0008165 A1 Jan. 14, 2021

(51) Int. Cl.

| | |
|---|---|
| ***A61K 38/18*** | (2006.01) |
| ***A61P 21/06*** | (2006.01) |
| ***A61K 39/085*** | (2006.01) |
| ***C07K 14/31*** | (2006.01) |
| ***C07K 14/495*** | (2006.01) |

(52) U.S. Cl.

CPC ........ *A61K 38/1841* (2013.01); *A61K 39/085* (2013.01); *A61P 21/06* (2018.01); *C07K 14/31* (2013.01); *C07K 14/495* (2013.01); *C07K 2319/40* (2013.01)

(58) Field of Classification Search

CPC ................................ A61K 38/00; A61K 8/64
See application file for complete search history.

(56) References Cited

U.S. PATENT DOCUMENTS

| | | | |
|---|---|---|---|
| 8,309,068 B2 | 11/2012 | Kambadur et al. |
| 9,089,150 B2 | 7/2015 | Chen et al. |
| 2013/0065820 A1 | 3/2013 | Bower et al. |

FOREIGN PATENT DOCUMENTS

| | | |
|---|---|---|
| CN | 102114239 A | 7/2011 |

OTHER PUBLICATIONS

Pearson, Curr Protoc Bioinformatics, 2013; 0 3: 1-9 (Year: 2013).*
Skolnick et al., Trends in Biotechnology, 2000; 18: 34-39 (Year: 2000).*
Moawad, Very Well Health, https://www.verywellhealth.com/muscle-atrophy-after-a-stroke-3146474; Mar. 28, 2022 (Year: 2022).*
Lisa-Ann Whittemore et al., Inhibition of myostatin in adult mice increases skeletal muscle mass and strength, Biochemical and Biophysical Research Communications, Jan. 24, 2003, pp. 965-971, vol. 300, Issue 4, Elsevier.
H.N. Peiris, M.D. Mitchell, The expression and potential functions of placental myostatin. Placenta, Nov. 2012, pp. 902-907, vol. 33, Issue 11, Elsevier.
Exotoxin [*Staphylococcus aureus*], NCBI Reference Sequence: WP_077156035.1, GenBank (GenBank database), Jan. 11, 2018 (Jan. 11, 2018), section "Origin".
Ren, K. et al. Enterotoxin H [*Staphylococcus aureus*], GenBank: AAA19777.1, GenBank (GenBank database), Apr. 16, 2001 (Apr. 16, 2001), section "Origin".

* cited by examiner

*Primary Examiner* — Brian Gangle
*Assistant Examiner* — Lakia J Jackson-Tongue
(74) *Attorney, Agent, or Firm* — Amin, Turocy & Watson, LLP

(57) ABSTRACT

Disclosed is a composition for promoting local muscle growth or slowing down or preventing local muscle atrophy, which composition contains a polypeptide in the C2 region of the enterotoxin Staphylococcus aureus and a myostatin polypeptide. By means of the composition, the defect in the prior art of only systemic muscle growth being possible has been overcome so as to achieve effects of promoting local muscle growth, or slowing down or preventing local muscle atrophy.

3 Claims, 11 Drawing Sheets

Specification includes a Sequence Listing.

SEQUENCE LISTING

```
<160> NUMBER OF SEQ ID NOS: 17

<210> SEQ ID NO 1
<211> LENGTH: 678
<212> TYPE: DNA
<213> ORGANISM: Staphylococcus aureus

<400> SEQUENCE: 1

tcaagtgagt ttactggtct gatggagaat atgaaagttt tatatgatga tcattatgta      60

tcagcaacta aagttatgtc tgtagataaa tttttggcac atgatttaat ttataacatt     120

agtgataaaa aactaaaaaa ttatgacaaa gtgaaaacag agttattaaa tgaagattta     180
```

-continued

```
gcaaagaagt acaaagatga agtagttgat gtgtatggat caaattacta tgtaaactgc    240

tatttttcat ccaaagataa tgtaggtaaa gttacaggtg gtaaaacttg tatgtatgga    300

ggaataacaa aatatgaagg aaaccacttt gataatggga acttacaaaa tgtacttata    360

agagtttatg aaaataaaag aaacacaatt tcttttgaag tgcaaactga taagaaaagt    420

gtaacagctc aagaactaga cataaaagct aggaattttt taattaataa aaaaaatttg    480

tatgagttta acagttcacc atatgaaaca ggatatataa aatttattga aaataacggc    540

aatacttttt ggtatgatat gatgcctgca ccaggcgata agtttgacca atctaaatat    600

ttaatgatgt acaacgacaa taaaacggtt gattctaaaa gtgtgaagat agaagtccac    660

cttacaacaa agaatgga                                                  678


<210> SEQ ID NO 2
<211> LENGTH: 45
<212> TYPE: DNA
<213> ORGANISM: Homo sapiens

<400> SEQUENCE: 2

gattttggac tcgactgtga tgagcactca acagaatctc gatgc                     45


<210> SEQ ID NO 3
<211> LENGTH: 954
<212> TYPE: DNA
<213> ORGANISM: artificial sequence
<220> FEATURE:
<223> OTHER INFORMATION: comprising SEC2m fragement and myostatin

<400> SEQUENCE: 3

tcaagtgagt ttactggtct gatggagaat atgaaagttt tatatgatga tcattatgta     60

tcagcaacta aagttatgtc tgtagataaa tttttggcac atgatttaat ttataacatt    120

agtgataaaa aactaaaaaa ttatgacaaa gtgaaaacag agttattaaa tgaagattta    180

gcaaagaagt acaaagatga agtagttgat gtgtatggat caaattacta tgtaaactgc    240

tatttttcat ccaaagataa tgtaggtaaa gttacaggtg gtaaaacttg tatgtatgga    300

ggaataacaa aatatgaagg aaaccacttt gataatggga acttacaaaa tgtacttata    360

agagtttatg aaaataaaag aaacacaatt tcttttgaag tgcaaactga taagaaaagt    420

gtaacagctc aagaactaga cataaaagct aggaattttt taattaataa aaaaaatttg    480

tatgagttta acagttcacc atatgaaaca ggatatataa aatttattga aaataacggc    540

aatacttttt ggtatgatat gatgcctgca ccaggcgata agtttgacca atctaaatat    600

ttaatgatgt acaacgacaa taaaacggtt gattctaaaa gtgtgaagat agaagtccac    660

cttacaacaa agaatggact cgaggatttt ggactcgact gtgatgagca ctcaacagaa    720

tctcgatgcg attttggact cgactgtgat gagcactcaa cagaatctcg atgcgatttt    780

ggactcgact gtgatgagca ctcaacagaa tctcgatgcg attttggact cgactgtgat    840

gagcactcaa cagaatctcg atgcgatttt ggactcgact gtgatgagca ctcaacagaa    900

tctcgatgcg attttggact cgactgtgat gagcactcaa cagaatctcg atgc          954


<210> SEQ ID NO 4
<211> LENGTH: 257
<212> TYPE: PRT
<213> ORGANISM: Staphylococcus aureus

<400> SEQUENCE: 4

Met Lys Lys Thr Ala Phe Thr Leu Leu Leu Phe Ile Ala Leu Thr Leu
```

-continued

```
1               5                   10                  15

Thr Thr Ser Pro Leu Val Asn Gly Ser Glu Lys Ser Glu Glu Ile Asn
            20                  25                  30

Glu Lys Asp Leu Arg Lys Lys Ser Glu Leu Gln Gly Thr Ala Leu Gly
        35                  40                  45

Asn Leu Lys Gln Ile Tyr Tyr Tyr Asn Glu Lys Ala Lys Thr Glu Asn
    50                  55                  60

Lys Glu Ser His Asp Gln Phe Leu Gln His Thr Ile Leu Phe Lys Gly
65                  70                  75                  80

Phe Phe Thr Asp His Ser Trp Tyr Asn Asp Leu Leu Val Asp Phe Asp
                85                  90                  95

Ser Lys Asp Ile Val Asp Lys Tyr Lys Gly Lys Lys Val Asp Leu Tyr
            100                 105                 110

Gly Ala Tyr Tyr Gly Tyr Gln Cys Ala Gly Gly Thr Pro Asn Lys Thr
        115                 120                 125

Ala Cys Met Tyr Gly Gly Val Thr Leu His Asp Asn Asn Arg Leu Thr
    130                 135                 140

Glu Glu Lys Lys Val Pro Ile Asn Leu Trp Leu Asp Gly Lys Gln Asn
145                 150                 155                 160

Thr Val Pro Leu Glu Thr Val Lys Thr Asn Lys Lys Asn Val Thr Val
                165                 170                 175

Gln Glu Leu Asp Leu Gln Ala Arg Arg Tyr Leu Gln Glu Lys Tyr Asn
            180                 185                 190

Leu Tyr Asn Ser Asp Val Phe Asp Gly Lys Val Gln Arg Gly Leu Ile
        195                 200                 205

Val Phe His Thr Ser Thr Glu Pro Ser Val Asn Tyr Asp Leu Phe Gly
    210                 215                 220

Ala Gln Gly Gln Tyr Ser Asn Thr Leu Leu Arg Ile Tyr Arg Asp Asn
225                 230                 235                 240

Lys Thr Ile Asn Ser Glu Asn Met His Ile Asp Ile Tyr Leu Tyr Thr
                245                 250                 255

Ser


<210> SEQ ID NO 5
<211> LENGTH: 266
<212> TYPE: PRT
<213> ORGANISM: Staphylococcus aureus

<400> SEQUENCE: 5

Met Tyr Lys Arg Leu Phe Ile Ser His Val Ile Leu Ile Phe Ala Leu
1               5                   10                  15

Ile Leu Val Ile Ser Thr Pro Asn Val Leu Ala Glu Ser Gln Pro Asp
            20                  25                  30

Pro Lys Pro Asp Glu Leu His Lys Ser Ser Lys Phe Thr Gly Leu Met
        35                  40                  45

Glu Asn Met Lys Val Leu Tyr Asp Asp Asn His Val Ser Ala Ile Asn
    50                  55                  60

Val Lys Ser Ile Asp Gln Phe Leu Tyr Phe Asp Leu Ile Tyr Ser Ile
65                  70                  75                  80

Lys Asp Thr Lys Leu Gly Asn Tyr Asp Asn Val Arg Val Glu Phe Lys
                85                  90                  95

Asn Lys Asp Leu Ala Asp Lys Tyr Lys Asp Lys Tyr Val Asp Val Phe
            100                 105                 110

Gly Ala Asn Tyr Tyr Tyr Gln Cys Tyr Phe Ser Lys Lys Thr Asn Asp
```

```
        115                 120                 125

Ile Asn Ser His Gln Thr Asp Lys Arg Lys Thr Cys Met Tyr Gly Gly
    130                 135                 140

Val Thr Glu His Asn Gly Asn Gln Leu Asp Lys Tyr Arg Ser Ile Thr
145                 150                 155                 160

Val Arg Val Phe Glu Asp Gly Lys Asn Leu Leu Ser Phe Asp Val Gln
                165                 170                 175

Thr Asn Lys Lys Lys Val Thr Ala Gln Glu Leu Asp Tyr Leu Thr Arg
            180                 185                 190

His Tyr Leu Val Lys Asn Lys Lys Leu Tyr Glu Phe Asn Asn Ser Pro
        195                 200                 205

Tyr Glu Thr Gly Tyr Ile Lys Phe Ile Glu Asn Glu Asn Ser Phe Trp
    210                 215                 220

Tyr Asp Met Met Pro Ala Pro Gly Asp Lys Phe Asp Gln Ser Lys Tyr
225                 230                 235                 240

Leu Met Met Tyr Asn Asp Asn Lys Met Val Asp Ser Lys Asp Val Lys
                245                 250                 255

Ile Glu Val Tyr Leu Thr Thr Lys Lys Lys
            260                 265


<210> SEQ ID NO 6
<211> LENGTH: 266
<212> TYPE: PRT
<213> ORGANISM: Staphylococcus aureus

<400> SEQUENCE: 6

Met Asn Lys Ser Arg Phe Ile Ser Cys Val Ile Leu Ile Phe Ala Leu
1               5                   10                  15

Ile Leu Val Leu Phe Thr Pro Asn Val Leu Ala Glu Ser Gln Pro Asp
            20                  25                  30

Pro Thr Pro Asp Glu Leu His Lys Ala Ser Lys Phe Thr Gly Leu Met
        35                  40                  45

Glu Asn Met Lys Val Leu Tyr Asp Asp His Tyr Val Ser Ala Thr Lys
    50                  55                  60

Val Lys Ser Val Asp Lys Phe Leu Ala His Asp Leu Ile Tyr Asn Ile
65                  70                  75                  80

Ser Asp Lys Lys Leu Lys Asn Tyr Asp Lys Val Lys Thr Glu Leu Leu
                85                  90                  95

Asn Glu Gly Leu Ala Lys Lys Tyr Lys Asp Glu Val Val Asp Val Tyr
            100                 105                 110

Gly Ser Asn Tyr Tyr Val Asn Cys Tyr Phe Ser Ser Lys Asp Asn Val
        115                 120                 125

Gly Lys Val Thr Gly Gly Lys Thr Cys Met Tyr Gly Gly Ile Thr Lys
    130                 135                 140

His Glu Gly Asn His Phe Asp Asn Gly Asn Leu Gln Asn Val Leu Ile
145                 150                 155                 160

Arg Val Tyr Glu Asn Lys Arg Asn Thr Ile Ser Phe Glu Val Gln Thr
                165                 170                 175

Asp Lys Lys Ser Val Thr Ala Gln Glu Leu Asp Ile Lys Ala Arg Asn
            180                 185                 190

Phe Leu Ile Asn Lys Lys Asn Leu Tyr Glu Phe Asn Ser Ser Pro Tyr
        195                 200                 205

Glu Thr Gly Tyr Ile Lys Phe Ile Glu Asn Asn Gly Asn Thr Phe Trp
    210                 215                 220
```

```
Tyr Asp Met Met Pro Ala Pro Gly Asp Lys Phe Asp Gln Ser Lys Tyr
225                 230                 235                 240

Leu Met Met Tyr Asn Asp Asn Lys Thr Val Asp Ser Lys Ser Val Lys
                245                 250                 255

Ile Glu Val His Leu Thr Thr Lys Asn Gly
            260                 265


<210> SEQ ID NO 7
<211> LENGTH: 227
<212> TYPE: PRT
<213> ORGANISM: Staphylococcus aureus

<400> SEQUENCE: 7

Glu Ser Gln Pro Asp Pro Thr Pro Asp Glu Leu His Lys Ser Ser Glu
1               5                   10                  15

Phe Thr Gly Thr Met Gly Asn Met Lys Tyr Leu Tyr Asp Asp His Tyr
            20                  25                  30

Val Ser Ala Thr Lys Val Met Ser Val Asp Lys Phe Leu Ala His Asp
        35                  40                  45

Leu Ile Tyr Asn Ile Ser Asp Lys Lys Leu Lys Asn Tyr Asp Lys Val
    50                  55                  60

Lys Thr Glu Leu Leu Asn Glu Asp Leu Ala Lys Lys Tyr Lys Asp Glu
65                  70                  75                  80

Val Val Asp Val Tyr Gly Ser Asn Tyr Tyr Val Asn Cys Tyr Phe Ser
                85                  90                  95

Ser Lys Asp Asn Val Gly Lys Val Thr Gly Gly Lys Thr Cys Met Tyr
            100                 105                 110

Gly Gly Ile Thr Lys His Glu Gly Asn His Phe Asp Asn Gly Asn Leu
        115                 120                 125

Gln Asn Val Leu Ile Arg Val Tyr Glu Asn Lys Arg Asn Thr Ile Ser
    130                 135                 140

Phe Glu Val Gln Thr Asp Lys Lys Ser Val Thr Ala Gln Glu Leu Asp
145                 150                 155                 160

Ile Lys Ala Arg Asn Phe Leu Ile Asn Lys Lys Asn Leu Tyr Glu Phe
                165                 170                 175

Asn Ser Ser Pro Tyr Glu Thr Gly Tyr Ile Lys Phe Ile Glu Asn Asn
            180                 185                 190

Gly Asn Thr Phe Trp Tyr Asp Met Met Pro Ala Pro Gly Asp Lys Phe
        195                 200                 205

Asp Gln Ser Lys Tyr Leu Met Met Tyr Asn Asp Asn Lys Thr Val Asp
    210                 215                 220

Ser Lys Ser
225


<210> SEQ ID NO 8
<211> LENGTH: 226
<212> TYPE: PRT
<213> ORGANISM: Staphylococcus aureus

<400> SEQUENCE: 8

Ser Ser Glu Phe Thr Gly Leu Met Glu Asn Met Lys Val Leu Tyr Asp
1               5                   10                  15

Asp His Tyr Val Ser Ala Thr Lys Val Met Ser Val Asp Lys Phe Leu
            20                  25                  30

Ala His Asp Leu Ile Tyr Asn Ile Ser Asp Lys Lys Leu Lys Asn Tyr
        35                  40                  45
```

-continued

```
Asp Lys Val Lys Thr Glu Leu Leu Asn Glu Asp Leu Ala Lys Lys Tyr
    50                  55                  60

Lys Asp Glu Val Val Asp Val Tyr Gly Ser Asn Tyr Tyr Val Asn Cys
65                  70                  75                  80

Tyr Phe Ser Ser Lys Asp Asn Val Gly Lys Val Thr Gly Gly Lys Thr
                85                  90                  95

Cys Met Tyr Gly Gly Ile Thr Lys Tyr Glu Gly Asn His Phe Asp Asn
            100                 105                 110

Gly Asn Leu Gln Asn Val Leu Ile Arg Val Tyr Glu Asn Lys Arg Asn
        115                 120                 125

Thr Ile Ser Phe Glu Val Gln Thr Asp Lys Lys Ser Val Thr Ala Gln
    130                 135                 140

Glu Leu Asp Ile Lys Ala Arg Asn Phe Leu Ile Asn Lys Lys Asn Leu
145                 150                 155                 160

Tyr Glu Phe Asn Ser Ser Pro Tyr Glu Thr Gly Tyr Ile Lys Phe Ile
                165                 170                 175

Glu Asn Asn Gly Asn Thr Phe Trp Tyr Asp Met Met Pro Ala Pro Gly
            180                 185                 190

Asp Lys Phe Asp Gln Ser Lys Tyr Leu Met Met Tyr Asn Asp Asn Lys
        195                 200                 205

Thr Val Asp Ser Lys Ser Val Lys Ile Glu Val His Leu Thr Thr Lys
    210                 215                 220

Asn Gly
225


<210> SEQ ID NO 9
<211> LENGTH: 258
<212> TYPE: PRT
<213> ORGANISM: Staphylococcus aureus

<400> SEQUENCE: 9

Met Lys Lys Phe Asn Ile Leu Ile Ala Leu Leu Phe Phe Thr Ser Leu
1               5                   10                  15

Val Ile Ser Pro Leu Asn Val Lys Ala Asn Glu Asn Ile Asp Ser Val
            20                  25                  30

Lys Glu Lys Glu Leu His Lys Lys Ser Glu Leu Ser Ser Thr Ala Leu
        35                  40                  45

Asn Asn Met Lys His Ser Tyr Ala Asp Lys Asn Pro Ile Ile Gly Glu
    50                  55                  60

Asn Lys Ser Thr Gly Asp Gln Phe Leu Glu Asn Thr Leu Leu Tyr Lys
65                  70                  75                  80

Lys Phe Phe Thr Asp Leu Ile Asn Phe Glu Asp Leu Leu Ile Asn Phe
                85                  90                  95

Asn Ser Lys Glu Met Ala Gln His Phe Lys Ser Lys Asn Val Asp Val
            100                 105                 110

Tyr Pro Ile Arg Tyr Ser Ile Asn Cys Tyr Gly Gly Glu Ile Asp Arg
        115                 120                 125

Thr Ala Cys Thr Tyr Gly Gly Val Thr Pro His Glu Gly Asn Lys Leu
    130                 135                 140

Lys Glu Arg Lys Lys Ile Pro Ile Asn Leu Trp Ile Asn Gly Val Gln
145                 150                 155                 160

Lys Glu Val Ser Leu Asp Lys Val Gln Thr Asp Lys Lys Asn Val Thr
                165                 170                 175

Val Gln Glu Leu Asp Ala Gln Ala Arg Arg Tyr Leu Gln Lys Asp Leu
            180                 185                 190
```

-continued

Lys Leu Tyr Asn Asn Asp Thr Leu Gly Gly Lys Ile Gln Arg Gly Lys
195 200 205

Ile Glu Phe Asp Ser Ser Asp Gly Ser Lys Val Ser Tyr Asp Leu Phe
210 215 220

Asp Val Lys Gly Asp Phe Pro Glu Lys Gln Leu Arg Ile Tyr Ser Asp
225 230 235 240

Asn Lys Thr Leu Ser Thr Glu His Leu His Ile Asp Ile Tyr Leu Tyr
245 250 255

Glu Lys

<210> SEQ ID NO 10
<211> LENGTH: 257
<212> TYPE: PRT
<213> ORGANISM: Staphylococcus aureus

<400> SEQUENCE: 10

Met Lys Lys Thr Ala Phe Ile Leu Leu Leu Phe Ile Ala Leu Thr Leu
1 5 10 15

Thr Thr Ser Pro Leu Val Asn Gly Ser Glu Lys Ser Glu Glu Ile Asn
20 25 30

Glu Lys Asp Leu Arg Lys Lys Ser Glu Leu Gln Arg Asn Ala Leu Ser
35 40 45

Asn Leu Arg Gln Ile Tyr Tyr Tyr Asn Glu Lys Ala Ile Thr Glu Asn
50 55 60

Lys Glu Ser Asp Asp Gln Phe Leu Glu Asn Thr Leu Leu Phe Lys Gly
65 70 75 80

Phe Phe Thr Gly His Pro Trp Tyr Asn Asp Leu Leu Val Asp Leu Gly
85 90 95

Ser Lys Asp Ala Thr Asn Lys Tyr Lys Gly Lys Lys Val Asp Leu Tyr
100 105 110

Gly Ala Tyr Tyr Gly Tyr Gln Cys Ala Gly Gly Thr Pro Asn Lys Thr
115 120 125

Ala Cys Met Tyr Gly Gly Val Thr Leu His Asp Asn Asn Arg Leu Thr
130 135 140

Glu Glu Lys Lys Val Pro Ile Asn Leu Trp Ile Asp Gly Lys Gln Thr
145 150 155 160

Thr Val Pro Ile Asp Lys Val Lys Thr Ser Lys Lys Glu Val Thr Val
165 170 175

Gln Glu Leu Asp Leu Gln Ala Arg His Tyr Leu His Gly Lys Phe Gly
180 185 190

Leu Tyr Asn Ser Asp Ser Phe Gly Gly Lys Val Gln Arg Gly Leu Ile
195 200 205

Val Phe His Ser Ser Glu Gly Ser Thr Val Ser Tyr Asp Leu Phe Asp
210 215 220

Ala Gln Gly Gln Tyr Pro Asp Thr Leu Leu Arg Ile Tyr Arg Asp Asn
225 230 235 240

Lys Thr Ile Asn Ser Glu Asn Leu His Ile Asp Leu Tyr Leu Tyr Thr
245 250 255

Thr

<210> SEQ ID NO 11
<211> LENGTH: 258
<212> TYPE: PRT
<213> ORGANISM: Staphylococcus aureus -continued

<400> SEQUENCE: 11

Met Lys Lys Leu Ser Thr Val Ile Ile Ile Leu Ile Leu Glu Ile Val
1 5 10 15

Phe His Asn Met Asn Tyr Val Asn Ala Gln Pro Asp Pro Lys Leu Asp
20 25 30

Glu Leu Asn Lys Val Ser Asp Tyr Lys Asn Asn Lys Gly Thr Met Gly
35 40 45

Asn Val Met Asn Leu Tyr Thr Ser Pro Pro Val Glu Gly Arg Gly Val
50 55 60

Ile Asn Ser Arg Gln Phe Leu Ser His Asp Leu Ile Phe Pro Ile Glu
65 70 75 80

Tyr Lys Ser Tyr Asn Glu Val Lys Thr Glu Leu Glu Asn Thr Glu Leu
85 90 95

Ala Asn Asn Tyr Lys Asp Lys Lys Val Asp Ile Phe Gly Val Pro Tyr
100 105 110

Phe Tyr Thr Cys Ile Ile Pro Lys Ser Glu Pro Asp Ile Asn Gln Asn
115 120 125

Phe Gly Gly Cys Cys Met Tyr Gly Gly Leu Thr Phe Asn Ser Ser Glu
130 135 140

Asn Glu Arg Asp Lys Leu Ile Thr Val Gln Val Thr Ile Asp Asn Arg
145 150 155 160

Gln Ser Leu Gly Phe Thr Ile Thr Thr Asn Lys Asn Met Val Thr Ile
165 170 175

Gln Glu Leu Asp Tyr Lys Ala Arg His Trp Leu Thr Lys Glu Lys Lys
180 185 190

Leu Tyr Glu Phe Asp Gly Ser Ala Phe Glu Ser Gly Tyr Ile Lys Phe
195 200 205

Thr Glu Lys Asn Asn Thr Ser Phe Trp Phe Asp Leu Phe Pro Lys Lys
210 215 220

Glu Leu Val Pro Phe Val Pro Tyr Lys Phe Leu Asn Ile Tyr Gly Asp
225 230 235 240

Asn Lys Val Val Asp Ser Lys Ser Ile Lys Met Glu Val Phe Leu Asn
245 250 255

Thr His

<210> SEQ ID NO 12
<211> LENGTH: 241
<212> TYPE: PRT
<213> ORGANISM: Staphylococcus aureus

<400> SEQUENCE: 12

Met Ile Asn Lys Ile Lys Ile Leu Phe Ser Phe Leu Ala Leu Leu Leu
1 5 10 15

Ser Phe Thr Ser Tyr Ala Lys Ala Glu Asp Leu His Asp Lys Ser Glu
20 25 30

Leu Thr Asp Leu Ala Leu Ala Asn Ala Tyr Gly Gln Tyr Asn His Pro
35 40 45

Phe Ile Lys Glu Asn Ile Lys Ser Asp Glu Ile Ser Gly Glu Lys Asp
50 55 60

Leu Ile Phe Arg Asn Gln Gly Asp Ser Gly Asn Asp Leu Arg Val Lys
65 70 75 80

Phe Ala Thr Ala Asp Leu Ala Gln Lys Phe Lys Asn Lys Asn Val Asp
85 90 95

Ile Tyr Gly Ala Ser Phe Tyr Tyr Lys Cys Glu Lys Ile Ser Glu Asn

```
            100                 105                 110

Ile Ser Glu Cys Leu Tyr Gly Gly Thr Thr Leu Asn Ser Glu Lys Leu
        115                 120                 125

Ala Gln Glu Arg Val Ile Gly Ala Asn Val Trp Val Asp Gly Ile Gln
    130                 135                 140

Lys Glu Thr Glu Leu Ile Arg Thr Asn Lys Lys Asn Val Thr Leu Gln
145                 150                 155                 160

Glu Leu Asp Ile Lys Ile Arg Lys Ile Leu Ser Asp Lys Tyr Lys Ile
                165                 170                 175

Tyr Tyr Lys Asp Ser Glu Ile Ser Lys Gly Leu Ile Glu Phe Asp Met
            180                 185                 190

Lys Thr Pro Arg Asp Tyr Ser Phe Asp Ile Tyr Asp Leu Lys Gly Glu
        195                 200                 205

Asn Asp Tyr Glu Ile Asp Lys Ile Tyr Glu Asp Asn Lys Thr Leu Lys
    210                 215                 220

Ser Asp Asp Ile Ser His Ile Asp Val Asn Leu Tyr Thr Lys Lys Lys
225                 230                 235                 240

Val


<210> SEQ ID NO 13
<211> LENGTH: 375
<212> TYPE: PRT
<213> ORGANISM: Homo sapiens

<400> SEQUENCE: 13

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
```

-continued

```
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375


<210> SEQ ID NO 14
<211> LENGTH: 15
<212> TYPE: PRT
<213> ORGANISM: Homo sapiens

<400> SEQUENCE: 14

Asp Phe Gly Leu Asp Cys Asp Glu His Ser Thr Glu Ser Arg Cys
1               5                   10                  15


<210> SEQ ID NO 15
<211> LENGTH: 344
<212> TYPE: PRT
<213> ORGANISM: Homo sapiens

<400> SEQUENCE: 15

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
```

-continued

```
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
    210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
    290                 295                 300

Gly Val Leu Leu Glu Val Lys His Ser Gly Ser Cys Asn Ser Ile Ser
305                 310                 315                 320

Glu Asp Thr Glu Glu Glu Glu Glu Asp Glu Asp Gln Asp Tyr Ser Phe
                325                 330                 335

Pro Ile Ser Ser Ile Leu Glu Trp
            340


<210> SEQ ID NO 16
<211> LENGTH: 288
<212> TYPE: PRT
<213> ORGANISM: Homo sapiens

<400> SEQUENCE: 16

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190
```

-continued

```
Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285


<210> SEQ ID NO 17
<211> LENGTH: 318
<212> TYPE: PRT
<213> ORGANISM: Artificial Sequence
<220> FEATURE:
<223> OTHER INFORMATION: comprising SEC2m fragement and myostatin
      fragment

<400> SEQUENCE: 17

Ser Ser Glu Phe Thr Gly Leu Met Glu Asn Met Lys Val Leu Tyr Asp
1               5                   10                  15

Asp His Tyr Val Ser Ala Thr Lys Val Met Ser Val Asp Lys Phe Leu
            20                  25                  30

Ala His Asp Leu Ile Tyr Asn Ile Ser Asp Lys Lys Leu Lys Asn Tyr
        35                  40                  45

Asp Lys Val Lys Thr Glu Leu Leu Asn Glu Asp Leu Ala Lys Lys Tyr
    50                  55                  60

Lys Asp Glu Val Val Asp Val Tyr Gly Ser Asn Tyr Tyr Val Asn Cys
65                  70                  75                  80

Tyr Phe Ser Ser Lys Asp Asn Val Gly Lys Val Thr Gly Gly Lys Thr
                85                  90                  95

Cys Met Tyr Gly Gly Ile Thr Lys Tyr Glu Gly Asn His Phe Asp Asn
            100                 105                 110

Gly Asn Leu Gln Asn Val Leu Ile Arg Val Tyr Glu Asn Lys Arg Asn
        115                 120                 125

Thr Ile Ser Phe Glu Val Gln Thr Asp Lys Lys Ser Val Thr Ala Gln
    130                 135                 140

Glu Leu Asp Ile Lys Ala Arg Asn Phe Leu Ile Asn Lys Lys Asn Leu
145                 150                 155                 160

Tyr Glu Phe Asn Ser Ser Pro Tyr Glu Thr Gly Tyr Ile Lys Phe Ile
                165                 170                 175

Glu Asn Asn Gly Asn Thr Phe Trp Tyr Asp Met Met Pro Ala Pro Gly
            180                 185                 190

Asp Lys Phe Asp Gln Ser Lys Tyr Leu Met Met Tyr Asn Asp Asn Lys
        195                 200                 205

Thr Val Asp Ser Lys Ser Val Lys Ile Glu Val His Leu Thr Thr Lys
    210                 215                 220

Asn Gly Leu Glu Asp Phe Gly Leu Asp Cys Asp Glu His Ser Thr Glu
225                 230                 235                 240

Ser Arg Cys Asp Phe Gly Leu Asp Cys Asp Glu His Ser Thr Glu Ser
                245                 250                 255

Arg Cys Asp Phe Gly Leu Asp Cys Asp Glu His Ser Thr Glu Ser Arg
            260                 265                 270
```

-continued

```
Cys Asp Phe Gly Leu Asp Cys Asp Glu His Ser Thr Glu Ser Arg Cys
        275                 280                 285

Asp Phe Gly Leu Asp Cys Asp Glu His Ser Thr Glu Ser Arg Cys Asp
    290                 295                 300

Phe Gly Leu Asp Cys Asp Glu His Ser Thr Glu Ser Arg Cys
305                 310                 315
```

COMPOSITION FOR PROMOTING LOCAL MUSCLE GROWTH OR SLOWING DOWN OR PREVENTING LOCAL MUSCLE ATROPHY AND USE THEREOF

FIELD OF INVENTION

The present invention relates to a composition, especially a composition for promoting local muscle growth. The present invention relates to a use for preparing a medicine, especially for promoting local muscle growth. The present invention relates to another composition, especially a composition for slowing or preventing local muscle atrophy. The present invention also relates to another use for preparing a medicine, especially for slowing or preventing local muscle atrophy.

BACKGROUND OF THE INVENTION

Myostatin is highly like other members of the transforming growth factor (TGF-β) family in terms of its sequence. The gene structure of myostatin includes three parts: (1) the N-terminal hydrophobic domain as a signal for protein secretion and release; (2) the highly conserved protein cleavage position RXRR; and (3) cysteine-rich C-terminal active domain. Many research reports indicate that the amino acid sequence of myostatin in vertebrates is highly conserved in the C-terminal active domain. Existing studies have proposed a monoclonal antibody JA16 with high specificity for myostatin (Whittemore et al., 2003, Biochemical and Biophysical Research Communications 300: 965-971). By analyzing the binding position of myostatin, it was found that the binding located at the 15 amino acid DFGLDCDEHSTESRC at the C-terminal of mouse myostatin, so that the C-terminal domain is an antigenic fragment.

However, the administration of anti-myostatin antibody would induce a systemic response. In 2016, Camporez et al. state the treatment of old mice with an anti-myostatin antibody would increase muscle mass, which in turn increases body weight. In addition, the clinical trial results in 2010 show that although the myostatin inhibitor ACE-031 can be used to increase systemic muscles and enhance muscle strength, the subjects have side effects such as spontaneous bleeding, nosebleeds, skin telangiectasias and headaches, so the clinical trial is terminated in 2011 due to negative phenomena. In particular, antibodies can cause the receptor immune system effects such as allergic reactions, chills, diarrhea, nausea and vomiting, itchy skin and other symptoms. In addition, anti-myostatin also cause systemic effects of the recipient's immune system, such as allergic reactions, chills, diarrhea, nausea and vomiting, and itchy skin. In 2012, H. N. Peiris (Placenta 33, 2012 902-907) pointed out there are some disadvantages to double-muscled cattle, namely the reduction in female calving and fertility. On the other hand, myostatin deficient mice ($Mstn^{-/-}$) are fertile; it speculates that myostatin may be a key regulator that contributes to placentation and the regulation of placental function throughout pregnancy.

Taiwan invention patent 1540968 discloses that the fusion of myostatin doubling fragment with an exotoxin region Ia fragment of *Pseudomonas aeruginosa* a polypeptide fragment or an antibody is effective for enhancing systemic immune response elicited. However, as known by technician, urea used for solubilizing inclusion bodies during proliferation would cause urea residual and protein refolding; refolding fragments may affect protein function. More importantly, the effects disclosed in this patent are still systemic responses, and therefore, myostatin antibodies in the prior art should be improved.

In addition, current research shows that enterotoxin secreted by Staphylococcus aureus can be divided into several types, including A, B, Cl, C2, D, E, and F, wherein SEA, SEB, SEC1 and SEC2 of Staphylococcal enterotoxin have similar molecular weights and high structural similarity, so they would all cause systemic immune responses, have the same clinical symptoms and side effects such as fever, blood pressure increasing.

Therefore, how to develop a medicine that only affects local muscles without causing a systemic response; the prior art needs to be improved.

SUMMARY OF THE INVENTION

In view of the disadvantages of prior art drug side effects, the object of the present invention is to provide a composition for promoting local muscle growth.

In one aspect, the invention relates to a composition for promoting local muscle growth, slowing or preventing local muscle atrophy, wherein the composition comprise a first polypeptide having at least 90% sequence similarity with a SEQ ID NO: 8; and a second polypeptide comprising from 1 to 10 repeat units of the sequence set forth in SEQ ID NO:14.

Preferably, the second polypeptide is a linear array epitope (LAE) of tandem repeated units, wherein the second polypeptide comprising from 1 to 10 repeat units of the sequence set forth in SEQ ID NO:14.

More preferably, the second polypeptide is a linear array of repeating antigens of a tandem repeat unit, wherein the second polypeptide comprises 6 repeat units of the sequence set forth in SEQ ID NO: 14.

Preferably, the substitution mutation of the first polypeptide corresponding to SEQ ID NO: 8 is selected from the group consisting of: T or L at position 7, G or E at position 9, Y or V at position 13, and H or Y at position 105.

Preferably, the first polypeptide is selected from the group consisting of set forth in SEQ ID NOs: 4, 5, 6, 7, 8, 9, 10, 11 and 12.

Preferably, the composition further comprises a linker between the first polypeptide and the second polypeptide, wherein the sequence of the composition is set forth in SEQ ID NO: 17.

In a preferred embodiment, the first polypeptide and the second polypeptide may be selected from the following:

Composition used in promoting muscle growth

| First polypeptide (polypeptide of *S. aureus* enterotoxin) | | Second polypeptide (epitope peptides at the C-terminus of myostatin) |
|---|---|---|
| SEA | SEQ ID NO: 4 | SEQ ID NO: 14, repeat from 1 to 10 times |
| SEB | SEQ ID NO: 5 | SEQ ID NO: 14, repeat from 1 to 10 times |
| SEC1 | SEQ ID NO: 6 | SEQ ID NO: 14, repeat from 1 to 10 times |
| SEC2 | SEQ ID NO: 7 | SEQ ID NO: 14, repeat from 1 to 10 times |
| SEC2m | SEQ ID NO: 8 | SEQ ID NO: 14, repeat from 1 to 10 times |
| SED | SEQ ID NO: 9 | SEQ ID NO: 14, repeat from 1 to 10 times |
| SEE | SEQ ID NO: 10 | SEQ ID NO: 14, repeat from 1 to 10 times |
| SEG | SEQ ID NO: 11 | SEQ ID NO: 14, repeat from 1 to 10 times |
| SEH | SEQ ID NO: 12 | SEQ ID NO: 14, repeat from 1 to 10 times |

In another aspect, the invention relates to a composition for promoting local muscle growth, slowing local muscle atrophy or preventing local muscle atrophy, wherein the composition comprises a polypeptide of *Staphylococcus aureus* enterotoxin and a myostatin polypeptide.

Preferably, the polypeptide of *S. aureus* enterotoxin is selected from the group consisting of *S. aureus* enterotoxins A, B, Cl, C2, D, E, F, G and H.

*S. aureus* Enterotoxins C2 (SEC2) has a molecular weight of 27 kDa and contains 239 amino acids. The SEC2 are transcribed to protein with 266 amino acid, and a molecular weight is 30 kDa. The SEC2 polypeptide is cleaved at alanine 27 to produce a mature toxin containing 239 amino acids with a molecular weight of 27 kDa. The N-terminal polypeptide sequencing determines the position of the cleavage of the message polypeptide in SEC2 and confirms the N-terminus of the mature toxin, thereby demonstrating that SEC2 is effective in enhancing the immune response elicited.

More preferably, the polypeptide sequence of the SEC2 having at least 90% sequence similarity with a SEQ ID NO: 8, for example, the substitution mutation of the first polypeptide corresponding to SEQ ID NO: 8 is selected from the group consisting of: T or L at position 7, G or E at position 9, Y or V at position 13, and H or Y at position 105.

Preferably, the myostatin polypeptide includes, but is not limited to, growth differentiation factor 8 (GDF8), follistatin or activin receptor type-2B (ACTR-IIB).

More preferably, the myostatin polypeptide is selected from the group consisting of GDF8 set forth in SEQ ID NO: 13, follistatin set forth in SEQ ID NO: 15, and ACTR-IIB set forth in SEQ ID NO: 16.

Preferably, the epitope polypeptide of myostatin is a linear array epitope (LAE) of tandem repeated units.

In another aspect, the invention is also related to a pharmaceutical composition for promoting local muscle growth, slowing local muscle atrophy, or preventing local muscle atrophy, which comprising a composition as previously described and a pharmaceutically acceptable carrier.

As used herein, "pharmaceutically acceptable carrier" includes, but is not limited to, water, alcohols, glycols, hydrocarbons (such as petroleum jelly and white petrolatum), wax (such as paraffin and yellow wax), preserving agents, antioxidants, solvent, emulsifier, suspending agent, decomposer, binding agent, excipient, stabilizing agent, chelating agent, diluent, gelling agent, preservative, lubricant, absorption enhancers, active agents, humectants, odor absorbers, fragrances, pH adjusting agents, occlusive agents, emollients, thickeners, solubilizing agents, penetration enhancers, anti-irritants, colorants, propellants, surfactants, adjuvants, and other carriers similar or suitable for use in the present invention.

As used herein, adjuvant includes, but is not limited to, alum precipitate, Freund's complete adjuvant, and monophosphoryl-lipid A/Trehalose dicorynomycolate adjuvant.

The pharmaceutical compositions of the present invention may exist in a variety of forms. These forms include, but are not limited to, liquid, semi-solid, and solid, wherein the liquid forms including, but not limited to, dispersions or suspensions; wherein semi-solids and solids forms including, but not limited to, tablets, pills, powders, liposomes, and suppositories. The preferred form depends on the intended mode of administration and therapeutic application. More preferably, the pharmaceutical composition is orally or infusible solution form.

In another aspect, the invention is related to a nucleic acid for promoting local muscle growth, slowing local muscle atrophy, or preventing local muscle atrophy, which encodes a composition consisting of the amino acid sequence set forth in SEQ ID NO:17.

In another aspect, the invention relates to a use of the composition as above described for manufacturing a pharmaceutical composition used in promoting local muscle growth by administering an effective dose of the pharmaceutical composition to local muscles of a recipient.

In a preferred embodiment of the present invention, the aforementioned composition is used to growth local muscle in mammals, including administration of a fusion protein of myostatin fragment and SEC2, thereby obtaining specific immune cells for anti-myostatin. The immune cells of the present invention can be introduced into other animals by the epitope of the myostatin fragment, and immunizing the cells by purified immune cells or epitopes to growth muscles in mammal. The immune cells of the present invention may be a plurality of B lymphocytes or T cell strains; preferably, the aforementioned immune cells are regulatory T cells.

In another aspect, the present invention relates to a use of the composition as above described for manufacturing a pharmaceutical composition used in preventing local muscle atrophy by administering an effective dose of the pharmaceutical composition to local muscles of a recipient. In one embodiment, the composition is applied to lateral leg muscles with damaged nerve on one lateral side to maintain muscle size and avoid nerve damage result in muscle atrophy. In another one embodiment, the composition is applied to lateral leg muscles with blocked nerve on one lateral side to maintain muscle size and avoid blocked nerve result in muscle atrophy.

The foregoing compositions and uses are suitable for use in animals. Preferably, it is suitable for vertebrates; more preferably, the myostatin of human, pig, cow, sheep, dog and poultry and waterfowl has been selected, and its amino acid sequence is highly conserved. Therefore, it can be assumed that the myostatin of the aforementioned animal has the same function; more preferably, the aforementioned mammal include, but are not limited to a human, a pig, a cow, a sheep ora dog.

The compositions of the present invention are suitable in a variety of conditions of muscle atrophy, which may be caused by drugs including, but not limited to, glucocorticoids such as cortisol, dexamethasonel, betamethasone, prednisone, methylprednisolone or prednisolone. Muscle atrophy can be caused by neurological trauma, degenerative, neuronal necrosis, metabolic or inflammatory neuropathy, such as Guillian-Barre syndrome, peripheral neuropathy, or exposure to environmental toxins.

In addition, muscle atrophy can be caused by muscle diseases including, but not limited to, myotonic dystrophy, congenital myopathies, familial periodic paralysis (FPP), metabolic muscle disease (caused by liver glycogen or lipid storage diseases), dermatomyositis, polymyositis, inclusion body myositis (IBM), myositis ossificans or rhabdomyolysis.

Muscle atrophy can also be caused by diseases including, but not limited to, motor neuron diseases (MND), spinal muscular atrophy (SMA), amyotrophic lateral sclerosis, juvenile spinal muscular atrophy (also known as SMA-III), myasthenia gravis (MG), paralysis due to stroke or spinal cord injury, bone fixation due to trauma, prolonged bed rest, autonomic inactivity, non-autonomous inactivity, metabolic stress or undernutrition, cancer, AIDS, fasting, thyroid disease, diabetes, central core disease (CCD), burns, chronic obstructive pulmonary disease, liver disease (such as fibrosis, cirrhosis), sepsis, renal failure, congestive heart failure, aging, space navigation, or spending a period of time in a zero-gravity environment.

In another aspect, the term "epitope" as used herein refers to a fragment capable of eliciting an immune response to produce a protein antigen, which can be observed by structure prediction or by selecting a protein fragment in animal. immune response.

In another aspect, the term "effective dose" as used herein refers to an amount effective to promote local muscle growth or to slow or prevent local muscle atrophy at dose during a period of time. The effective dose for promoting local muscle growth can be learned in promoting local muscle growth test (Example 1); the effective dose for slowing or preventing local muscle atrophy can be learned in slowing or preventing local muscle atrophy test (Examples 2 and 3).

Since the epitope is a small polypeptide fragment, the immune response in animal test induced by the small polypeptide fragment may less ideal. Preferably, a linear array epitope (LAE) comprising a tandem repeat unit can improve the immune response. In addition, bacterial toxins can be used to delivery antigen by using eliminated toxin as a delivery system to enhance the overall immune response with the properties of the toxin. In one aspect, the linear array of repeat units of the epitope of the C-terminus of the myostatin of the present invention is fused to SEC2.

A host cell can produce above nucleic acid. The embodiments of host cells include, but are not limited to *Escherichia coli*, insect cells, plant cells, yeast cells, and mammalian cells. The nucleic acid molecule can be used to express a polypeptide or fusion protein described herein the present invention, which can be operably linked to a multiple cloning site (MCS) of a suitable vector to produce the polypeptide or fusion protein.

The embodiments of vector include, but are not limited to plasmids. Preferably, the vector comprises a promoter, an enhancer, a multiple cloning site, etc., while the nucleic acid molecule is ligated to a multiple cloning site of a suitable vector, the expression vector can be introduced into a host cell to produce a polypeptide or fusion protein as described herein. The host cell includes, but is not limited to, *Escherichia coli, Bordetella pertussis, Bacillus cereus*, African green monkey kidney cells, Haemophilus, fungi or yeast.

An advantage of the present invention is that it is a breakthrough and no precedent in the field of promoting local muscle growth by the composition comprising the SEC2 polypeptide sequence and the myostatin with epitope polypeptide of C-terminus. Further, it is unexpectedly found that the lateral leg muscles with damaged or blocked nerve can maintain muscle size by administering the composition to the lateral leg muscles. It will contribute to avoid local muscle atrophy effectively in clinical patients suffer damaged or blocked nerve.

BRIEF DESCRIPTION OF THE DRAWINGS

The present disclosure will become more fully understood from the detailed description and the accompanying drawings, in which:

FIG. 4 (A) is a longitudinal section scan of the low-dose control group, and the muscle volume is calculated by the area between the upper and lower dashed lines; FIG. 4 (B) is a longitudinal section scan of the medium-dose control group, and the muscle volume is calculated by the area between the upper and lower dashed lines; FIG. 4 (C) is a longitudinal section scan of the high-dose control group, and the muscle volume is calculated by the area between the upper and lower dashed lines; FIG. 4 (D) is a cross sectional scan of the low-dose control group; FIG. 4 (E) is a cross sectional scan of the medium-dose control group; FIG. 4 (F) is a cross sectional scan of the high-dose control group; FIG. 4 (G) is a longitudinal section scan of the low-dose experimental group, and the muscle volume is calculated by the area between the upper and lower dashed lines; FIG. 4 (H) is a longitudinal section scan of the medium-dose experimental group, and the muscle volume is calculated by the area between the upper and lower dashed lines; FIG. 4 (I) is a longitudinal section scan of the high-dose experimental group, and the muscle volume is calculated by the area between the upper and lower dashed lines; FIG. 4 (J) is a cross sectional scans of the low-dose experimental group; FIG. 4 (K) is a cross sectional scan of the medium-dose experimental group; FIG. 4 (L) is a cross sectional scan of a high-dose experiment group.

FIGS. 10 (D) to 10(F) are respectively 50 ng (low-dose), 500 ng (medium-dose) and 5000 ng (high-dose) experimental group.

DETAILED DESCRIPTION OF THE PREFERRED EMBODIMENTS

Figure 1:
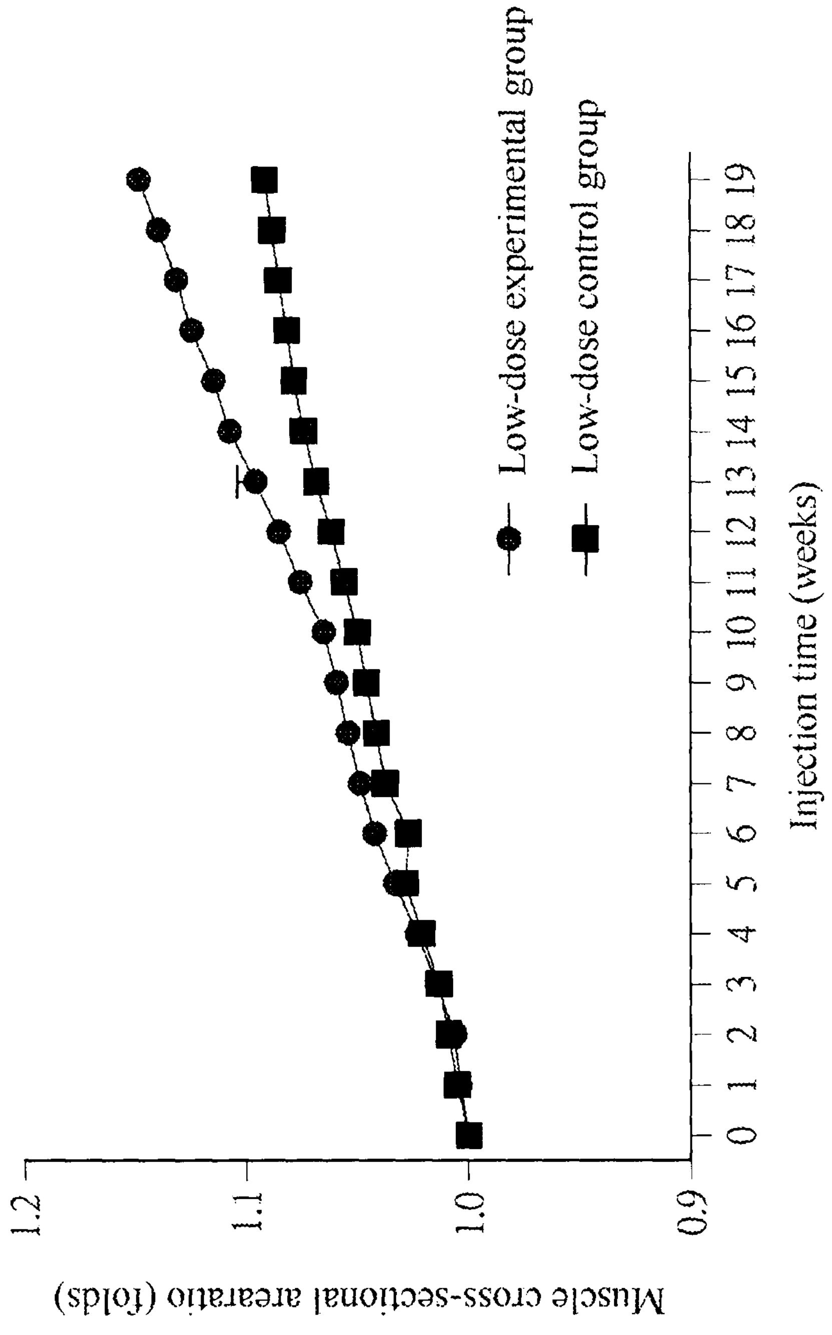
FIG. 1 is a line graph related to the ratio of muscle cross-sectional area of a low-dose experimental group and a low-dose control group of the present invention. The low-dose experimental group is indicated by a broken line indicating ● and the low-dose control group was indicated by a broken line indicating ■.

The technical means adopted by the present invention for achieving the intended purpose of the invention are further described below in conjunction with the drawings and preferred embodiments of the invention.

Preparation Example 1

Preparation of the Composition Comprising an SEC2 Fragment and a Myostatin Fragment The fusion protein used in this embodiment was pET expression system of *Escherichia coli*; preferably, the expression system was pET-28a. Wherein the first polypeptide "SEC2m" was a SEC2 having a point mutation, the nucleic acid sequence was set forth in SEQ ID NO: 1, and the protein sequence was set forth in SEQ ID NO: 8, wherein the point mutation was: 7T>L, 9G>E, 13Y>V, and 105H>Y. The second polypeptide "Myo epitope" was epitope of myostatin, which was 15 amino acids with 6 repeats in C-terminal and highly conserved in multiple species (as set forth in SEQ ID NO: 14). the nucleic acid sequence of a single fragment was set forth in SEQ ID NO :2. The gene sequence located in the multiple cloning site (MCS) of the pET vector from the N-terminus was SEC2m, linker and Myo epitope, which was set forth in SEQ ID NO: 3.

35 L fermentation culture process was established, to culture *Escherichia coli* BL21(DE3) strain containing the fragment set forth in SEQ ID NO: 3 in a 50 L fermentation tank 4 tubes of 5 mL bacterial strain cultured overnight with LB/Ampicillin medium at 37° C. were respectively inoculated into 0.2 L LB/Ampicillin medium and a total of 1 L were shook and cultured at 37° C. to OD600 of 0.3, and then added into 35 L medium for culturing, and sampled for determining OD600 every two hours to monitor the variations of the growth curve. Suitable time points were further selected according to the growth curve, IPTG having a final concentration of 0.1 mM was added to induce *Escherichia coli* to express the fusion protein at a high level, shook and cultured at 37° C. for 3 hours, and centrifuged to recover the bacteria. The expression of the fusion protein was determined through SDS-PAGE and western blotting, to determine the optimum 35 L fermentation conditions. Generally, the fusion polypeptide expressed by *Escherichia coli* BL21 (DE3) was subjected to extraction and isolation of the fusion polypeptide after cell lysis, and then obtaining a composition set forth in SEQ ID NO: 17. The extraction and isolation were conventional techniques.

Example 1

Promoting Local Muscle Growth Test

The mice used in the animal experiments of this example were 8 week old (12 month old) female mice of the C57BL/6 strain, and a total of 9 mice in the control group and the experimental group. The period of experiment was 6 months. When the mice grew to 12 months, they were feed with high-fat diets and raised water with high fructose syrup. Feed and water would be replaced every two days to avoid deterioration. The feed was stored at −20° C., and the high fructose syrup was stored at 4° C.; the body weight was measured every two weeks. After 6 months of feeding, the experimental animals began intramuscular injection of the composition once a week. The composition obtained from preparation Example 1 diluted into a different concentration by physiological saline was injected into the muscles of the left hind calf of the mice into different doses as the experimental group, and the right lower hind calf was injected with saline. The experimental groupings were shown in Table 1.

The grouping of animal experiment and the administration method of composition of the present invention

| Group | The dose of each administered to each mouse | The volume of intramuscular injection | Amount of animal | Frequency |
|---|---|---|---|---|
| Low-dose | 50 ng | 10 μL | 3 | once a week |
| Medium-dose | 500 ng | 10 μL | 3 | once a week |
| High-dose | 5000 ng | 10 μL | 3 | once a week |

The collection of experimental data was measured weekly by a vernier scale, measuring the long diameter (a), short diameter (b) and body weight of the muscle; the measurement position was the position of the injection. The approximately cross-sectional area was calculated as the ellipse area: a×b×3.14, and the muscle volume was calculated by the area between the upper and lower dashed lines in FIG. 4 (A), FIG. 4 (B), FIG. 4 (C), FIG. 4 (G), FIG. 4 (H), FIG. 4 (I).

Figure 2:
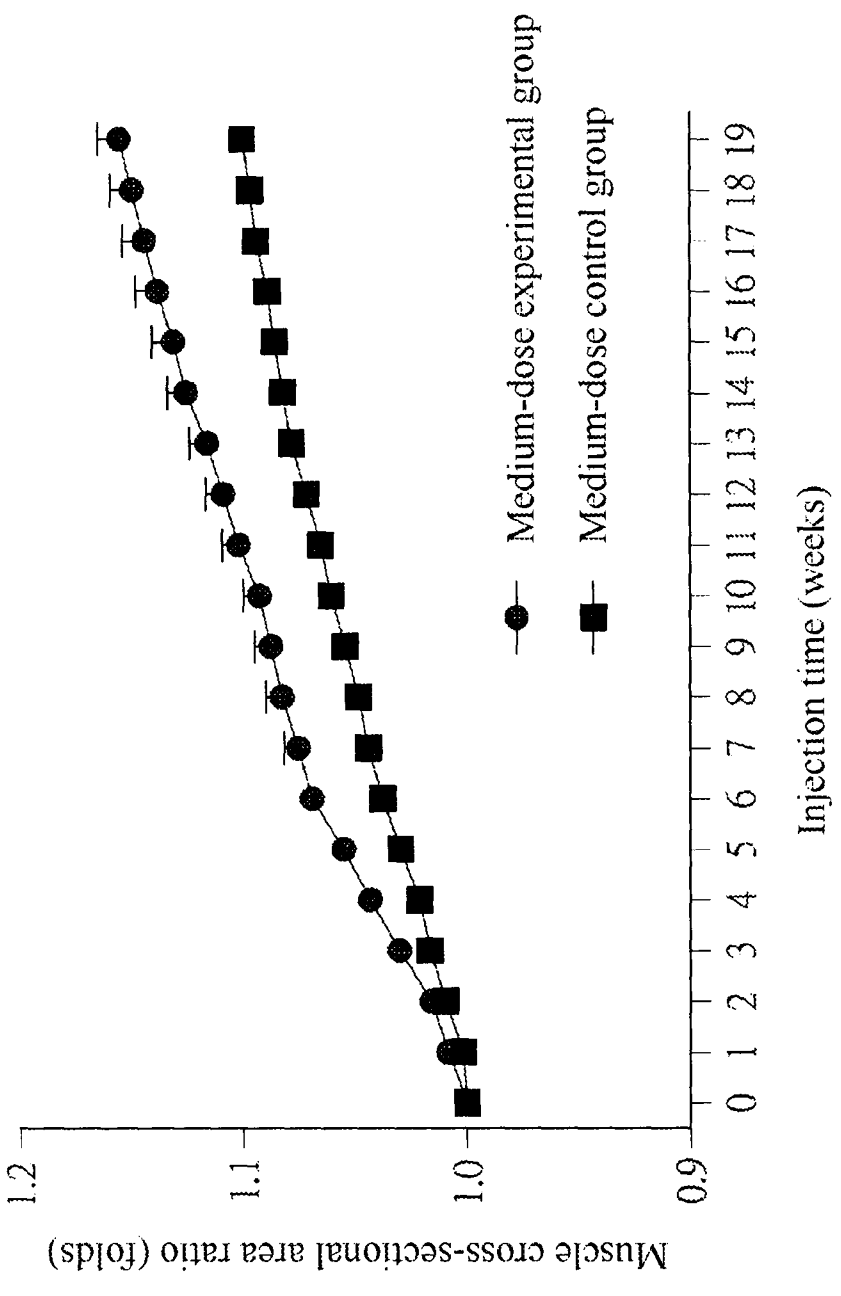
FIG. 2 is a line graph related to the ratio of the muscle cross-sectional area of medium dose experimental group and a medium-dose control group of the present invention. The medium-dose experimental group is indicated by a broken line indicating ●, and the medium-dose control group is indicated by a broken line indicating ■.
Figure 3:
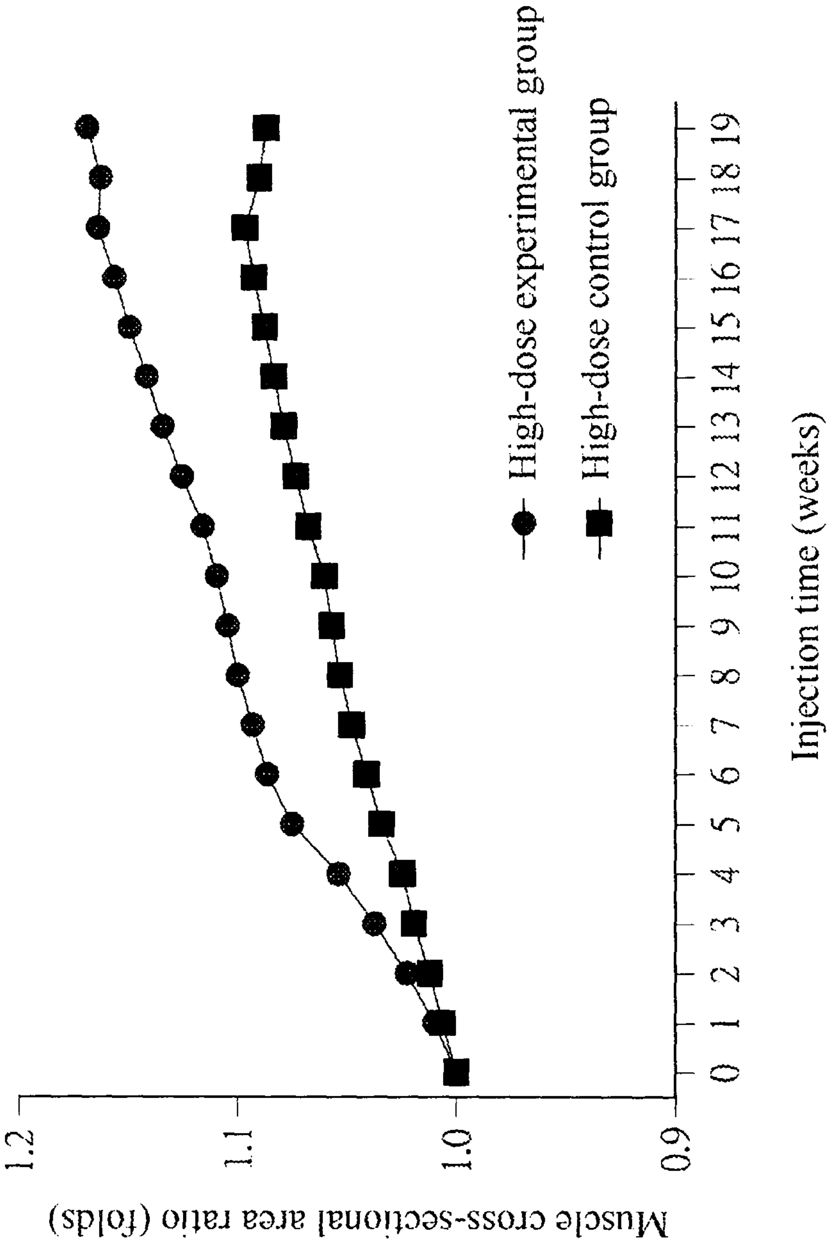
FIG. 3 is a line graph related to the ratio of the muscle cross-sectional area of the high-dose experimental group of the present invention compared with the high-dose control group. The high-dose experimental group is indicated by a broken line indicating ●, and the high-dose control group is indicated by a broken line indicating ■.

(1) Comparing the muscle cross-sectional area of the experimental group (left hind calf) and the control group (right hind calf) after injecting the composition of the present invention As shown in FIGS. 1 to 3, each experimental group was compared with the control group at the week 19, wherein the cross-sectional area of the calf injected with the high-dose composition was increased by 8.19% compared with the high-dose control group. The cross-sectional area of the calf with the medium-dose composition increased by 5.5% compared to the medium-dose control group. The cross-sectional area of the low-dose composition was increased by 5.67% compared to the low-dose control group.

Figure 4:
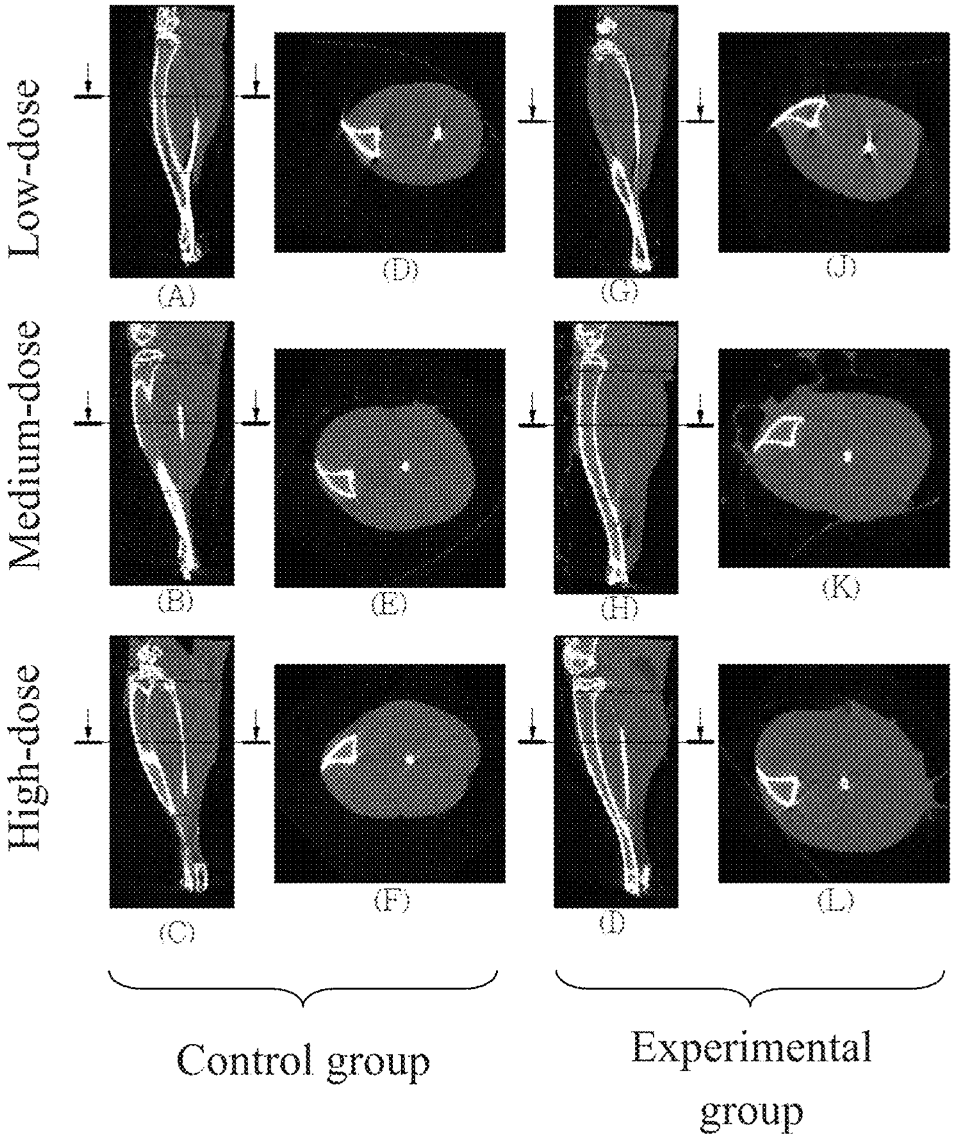
FIG. 4 is a longitudinal sectional view and a cross-sectional scan of the computerized tomography of the mouse hind leg of the present invention, each cross-sectional scan is a cross section of the cross-sectional line of the corresponding longitudinal section scan.

(2) Comparing the muscle volume of the experimental group (left hind calf) and the control group (right hind calf) after injecting the composition of the present invention Referring to FIG. 4, a longitudinal cross-sectional scan and a cross-sectional scan of the computerized tomography of the mouse hind calf, each cross-sectional scan is a cross-section of the cross-sectional line of the corresponding longitudinal section scan. the range of the muscle volume was calculated by the area between the dashed lines in FIG. 4 (A), FIG. 4 (B), FIG. 4 (C), FIG. 4 (G), FIG. 4 (H), FIG. 4 (I), wherein the muscle volume was obtained by integrating each cross-sectional area. The experiment was terminated after administration until 19 weeks. The mice were sacrificed and their calves were fixed with 10% formalin, and then subjected to computed tomography.

Figure 5:
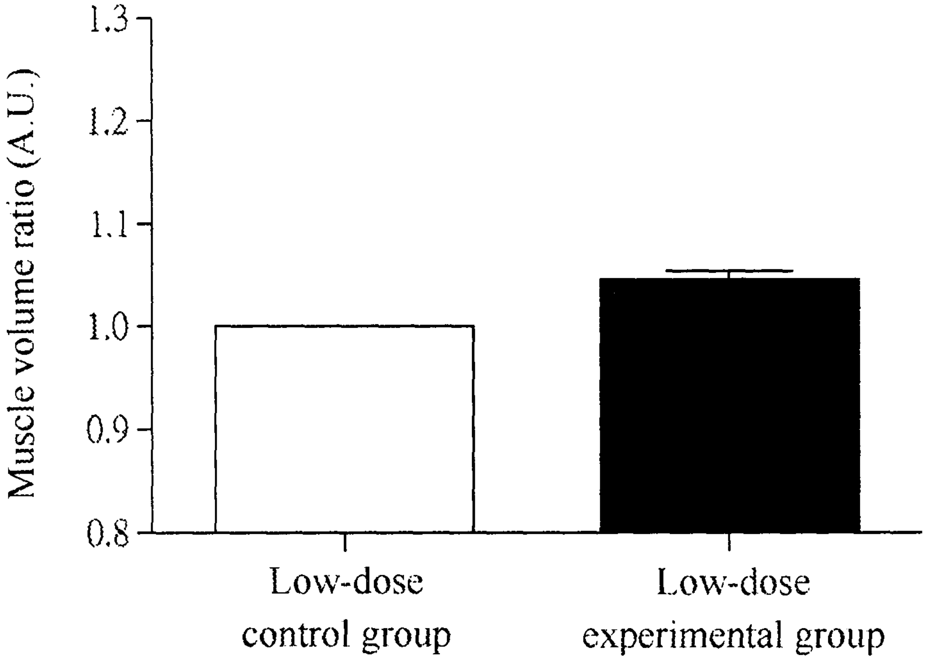
FIG. 5 is a bar graph of the volume ratio of the mice hind leg of the low-dose control group and the low-dose experimental group of the present invention; A.U. indicates an arbitrary unit.
Figure 6:
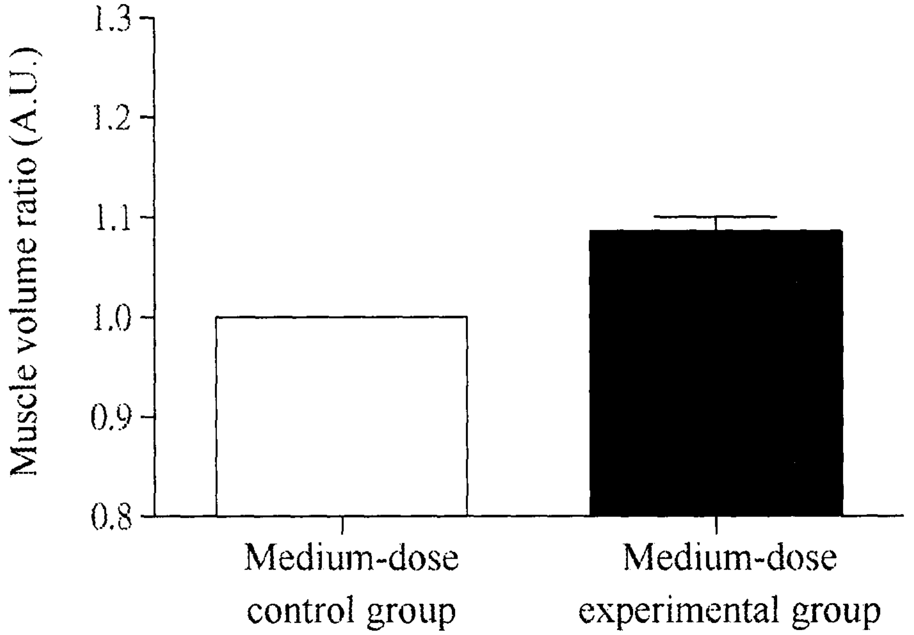
FIG. 6 is a bar graph of the volume ratio of the mice hind leg of the medium-dose control group and the medium-dose experimental group of the present invention; A.U. indicates an arbitrary unit.
Figure 7:
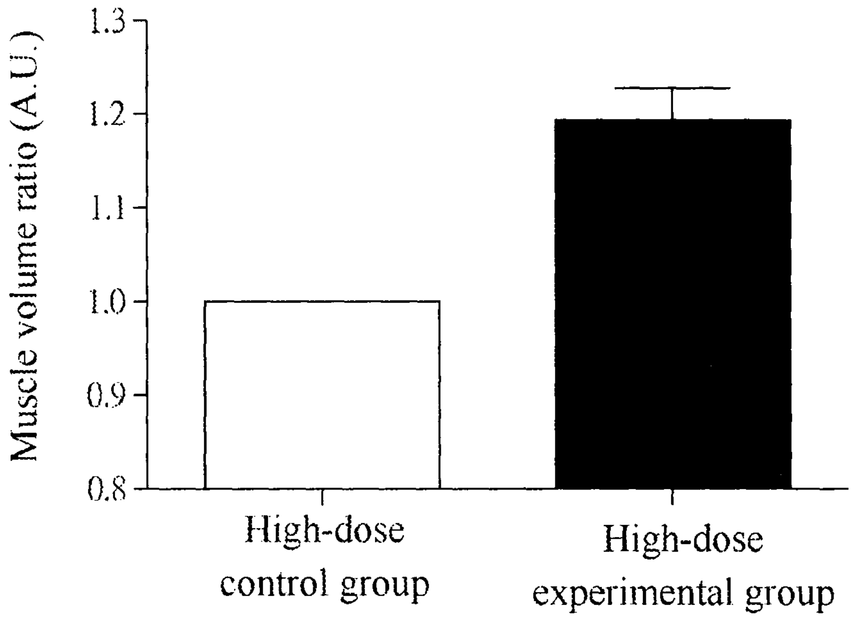
FIG. 7 is a bar graph of the volume ratio of the mice hind leg of the high-dose control group and the high-dose experimental group of the present invention; A.U. indicates an arbitrary unit.

Referring to FIGS. 5 to 7, the muscle volume of the low-dose experimental group increased by 4.6% compared with the low-dose control group; the muscle volume of the medium-dose experimental group increased by 8.5% compared with the middle-dose control group; the muscle volume of the high-dose experimental group increased by 19.2% compared with the high-dose control group. Since the test was based on the muscle of the left hind calf as the experimental group, and the right hind calf as the control group in an identical mouse, the results showed that the injection of the composition of the present invention into the left calf only causes the left calf muscle to grow on the side. On the other side (right side), the muscles of the calf did not grow, so that the composition of the present invention produced muscle growth only by the local administration, but did not cause systemic muscle enlargement.

(3) Measuring the thickness of the myofilament fiber after the injection in the experimental group (left hind calf) and the control group (right hind calf)

Figure 8:
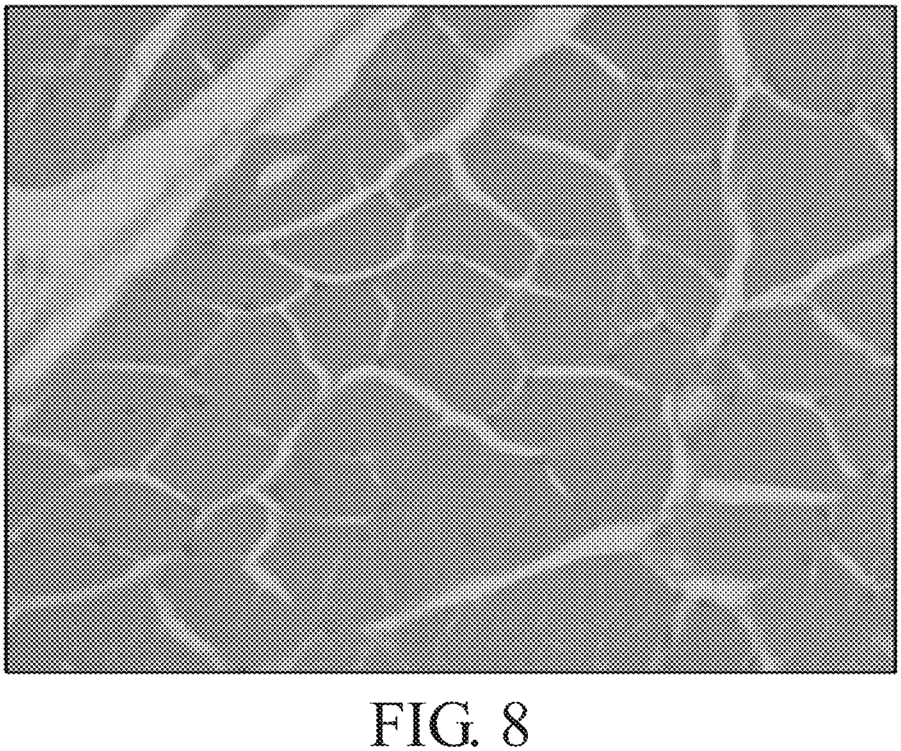
FIG. 8 is a staining diagram of hematoxylin-eosin (H-E) tissue staining of the mice calf muscle fibers of the high-dose control group of the present invention.
Figure 9:
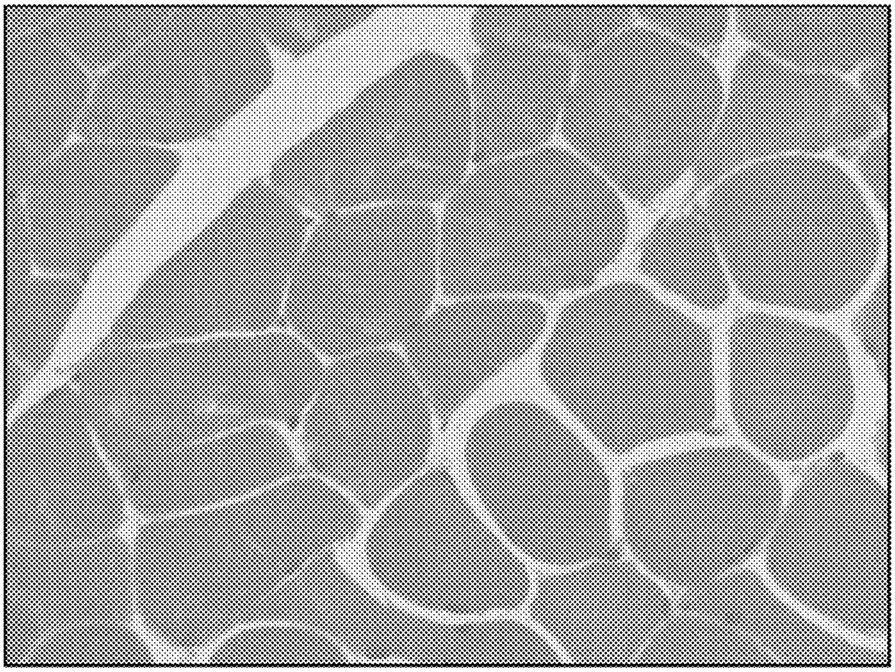
FIG. 9 is a staining diagram of the H-E tissue staining of the mice calf muscle fibers of the high-dose experimental group of the present invention.

At week 19, the calf bones of the mice were taken out after scanning computerized tomography and sacrificing, and then the muscles were embedded in paraffin and sectioned, and the thickness of the myofilament fibers was compared by H-E tissue staining. Referring to FIG. 8 and FIG. 9, FIG. 8 was the muscle fiber of the hind calf of the high-dose group as the control group, and FIG. 9 was the muscle fiber of the hind calf of the high-dose group as the experimental group. The muscle fiber of the high-dose group (the experimental group) was significantly increased compared to the control group.

(4) Measurement of the distribution of myostatin content after injection of the experimental group (left hind calf) and the control group (right hind calf)

Figure 10:
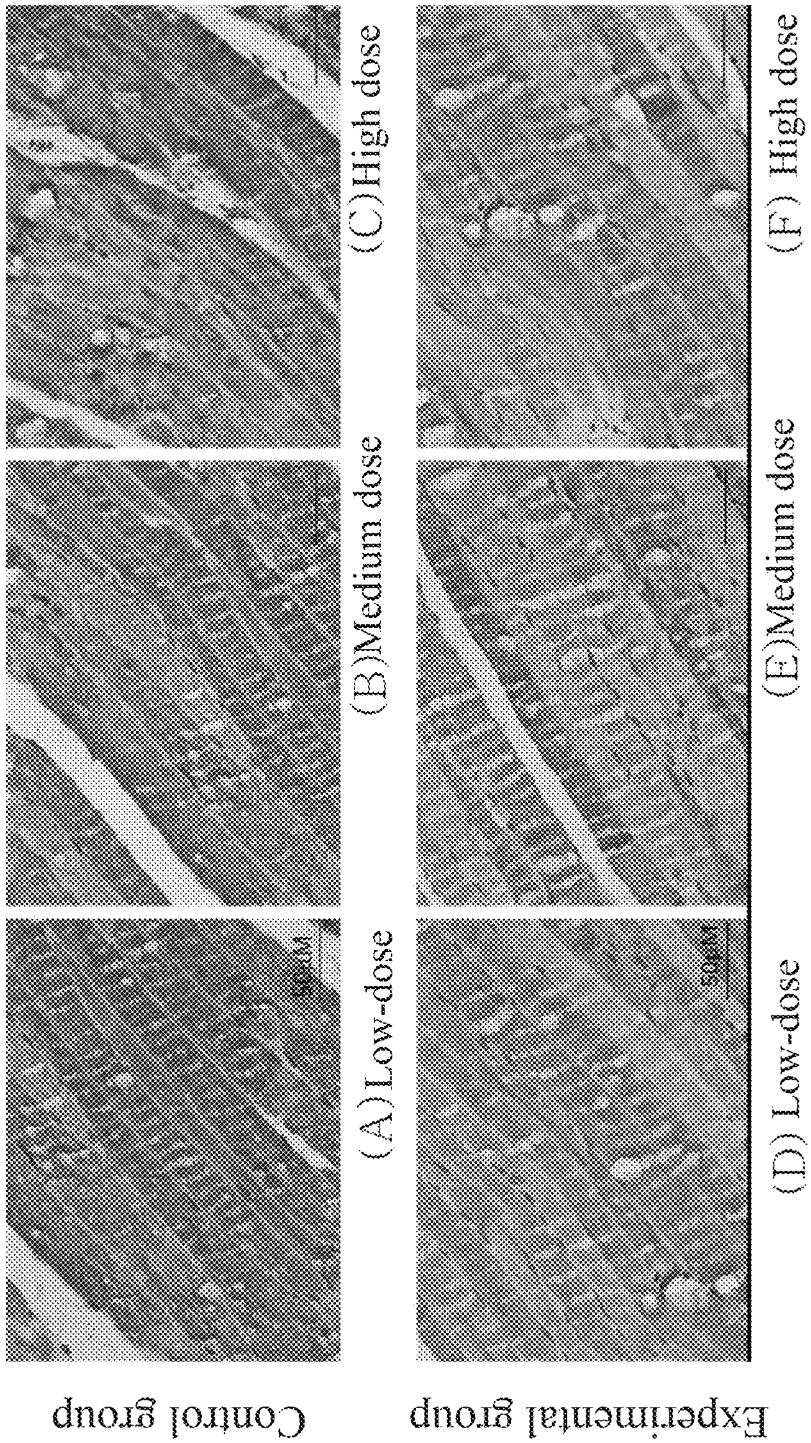
FIG. 10 is a diagram of immunohistochemical staining of mice calf muscle fibers administered myostatin of the present invention; wherein FIGS. 10 (A) to 10 (C) are control groups.

At week 19, the calf bones of the mice were taken out after scanning computerized tomography and sacrificing, and then the muscles were embedded in paraffin and sectioned, and the distribution of myostatin content was observed with myostatin antibody by immunohistochemical staining (IHC). Referring to FIG. 10, myostatin can be significantly stained in the different doses of the control groups (left posterior calf) as shown in FIG. 10 (A), FIG. 10 (B), and FIG. 10 (C). In contrast, the expressions of myostatin were significantly inhibited in the low dose, the medium dose, or the high dose experimental group (right hind calf) as shown in FIG. 10 (D), FIG. 10 (E), and FIG. 10 (F). That is, regardless of the low, the medium or the high dose group, the right hind calf (ie, the control group) had a high concentration of myostatin and the right hind calf muscle did not become significantly larger compared to the muscle of the left hind calf in an identical mouse. In other words, myostatin of the left hind calf (ie, the experimental group) was inhibited by the composition of the present invention, so that the myostatin concentration was low, and the muscle of the left hind calf in the identical mouse was enlarged, that is, the composition of the present invention has the effect of increasing local muscle mass, but not affected by systemic blood circulation.

Figure 11:
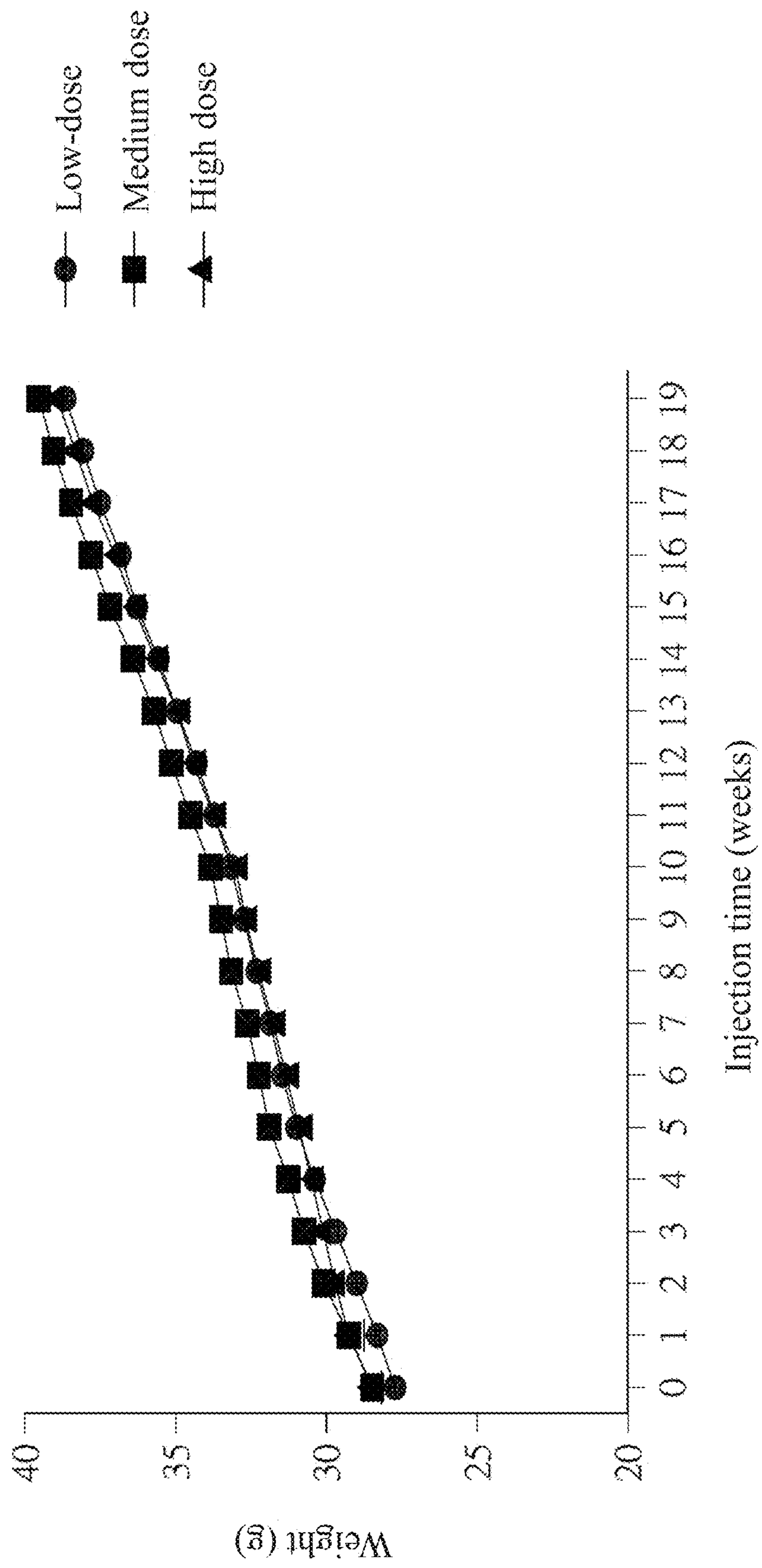
FIG. 11 is a line graph related to the weight change after administering of the composition in low-dose, medium-dose and high-dose experimental group of the present invention. wherein the low-dose experimental group is indicated by a broken line indicating ●, the medium-dose experimental group is indicated by a broken line indicating ■, and the high-dose experimental group is indicated by a broken line indicating ▲.

(5) Comparing changes in body weight after injection of the low-dose, the medium-dose or the high doses of the composition of the present invention Body weight was measured at week 19, as shown in FIG. 11, there was no significant difference in body weight either in the low-dose, the medium-dose or the high-dose group after administration of the composition of the present invention. Therefore, this test showed that the composition of the present invention only increases the muscle at the local administration site and does not increase systemic muscle.

Example 2

Slowing or Preventing Local Muscle Atrophy Caused by Nerve Damaged Test

10 ICR mice (eight weeks old, purchased from Lesco Biotech Co., Ltd.) fed in normal diet for 1 week to 2 weeks, and then divided into 2 groups (5 mice in each group). In the day I, the left leg sciatic nerve of each group of mice (no sciatic nerve injury in the right leg of each group) were undergone sciatic nerve injury surgery to caused sciatic nerve injury. The mice were sacrificed on day 28. The control group was the mice that underwent sciatic nerve injury surgery to destroy the sciatic nerve of the left leg, but did not receive any administration. The experimental group was the mice that underwent sciatic nerve injury surgery to destroy that the sciatic nerve of the left leg and each mouse in the experimental group was intramuscularly injected on days 1, 3, 7, and 14 with 1000 ng composition obtained from the preparation example 1 of the present invention. The level of muscle atrophy was observed to evaluate the effect of the composition of the present invention on slowing or preventing muscle atrophy.

The sciatic nerve injury surgery was performed under abdominal anesthesia. The body hair was removed from the knee to the buttocks of the mouse, fixed the mouse's legs and disinfected the surgical site with alcohol cotton, found the position of the thigh femur and opened an incision near the buttocks parallel femur. After the muslce layer was peeled off, a sciatic nerve parallel to the femur would be seen. Picking up the sciatic nerve and injuring by special tools, and then returning the sciatic nerve to the original position and observing the wound healing, gait changes and overall status of the mouse daily after suturing the skin. The objective was designed to mimic the state of nerve injury.

Figure 12:
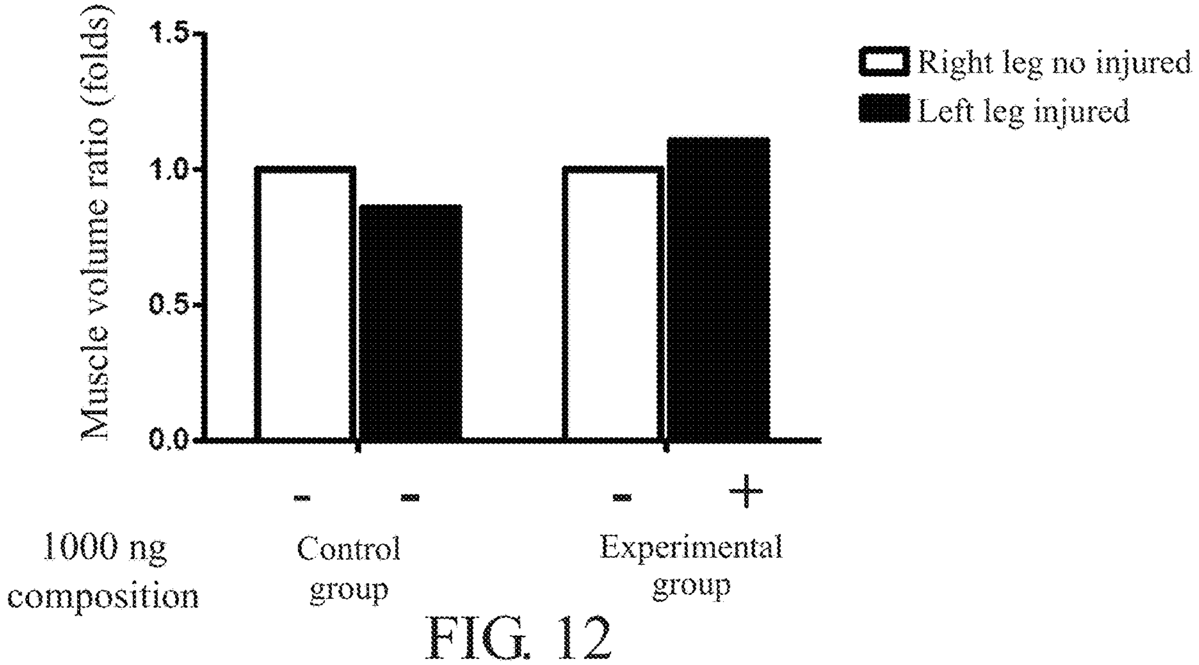
FIG. 12 is a bar graph related to the ratio of muscle volume after damaging sciatic nerve and then administered 1000 ng composition of the present invention in low-dose, medium-dose and high-dose experimental group of the present invention; wherein the sciatic nerve of the left leg was injured, but the sciatic nerve of right leg was not damaged.

The results showed that on the day 28, the volume of the left thigh muscle of one of the control group mice was about 1373 mm3, and the volume of the right thigh muscle was about 1595 mm3. Because the mice did not undergo sciatic nerve injury surgery on their right thighs, so the volume of the right thigh muscle can be regarded as the baseline and the ratio is 1. The volume ratio of the left thigh muscle is the volume of the left thigh muscle divided by the volume of the right thigh muscle (as shown in the control group in FIG. 12). It showed that the muscles of the left thigh compared to the right thigh was atrophy in the control group. The volume of the left thigh muscle of one of the experimental group mice was about 1888 mm3, and the volume of the right thigh muscle was about 1705 mm3. The volume of the right thigh muscle was as the baseline ratio 1. The volume ratio of the left thigh muscle is the volume of the left thigh muscle divided by the volume of the right thigh muscle (as shown in the experimental group in FIG. 12). Although the left thigh of the mouse underwent the sciatic nerve injury surgery, the left leg muscles are not atrophied due to the administration of the composition of the present invention.

Figure 13:
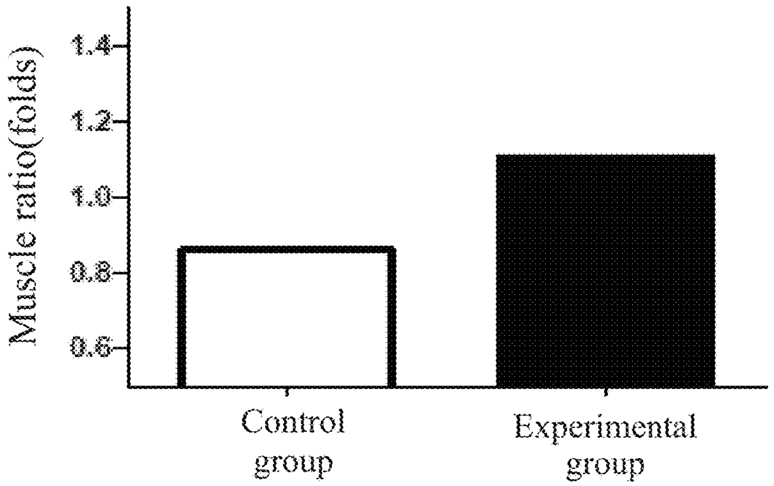
FIG. 13 is a bar graph related to the muscle ratio obtained from the left leg muscle volume ratio divided by the right leg muscle volume ratio in the control group, and that in the experimental group of FIG. 12.

As shown in FIG. 13, the left thigh/right thigh muscle volume ratio of the control group was about 0.86 (less than 1 means atrophy); the left thigh/right thigh muscle volume ratio of the experimental group was about 1.11, so the experimental group compared The control group exhibits a phenomenon of maintaining a muscle volume by administering the composition of the present invention. Thus, in the case of nerve damage, by administering the composition of the present invention, local muscle atrophy or even the maintenance of the original muscle volume can be reduced or relieved.

Example 3

Slowing or Preventing Local Muscle Atrophy Caused by Nerve Truncation

10 ICR mice (eight weeks old, purchased from Lesco Biotech Co., Ltd.) fed in normal diet for 1 week to 2 weeks, and then divided into 2 groups (5 mice in each group). In the day 1, the mice were divided into a control group, an experimental group A, and an experimental group B. The control group was the mice that underwent nerve truncation on their sciatic nerve of the left leg, but did not administer the composition of the present invention. The experimental group A was the mice that underwent nerve truncation on their sciatic nerve of the left leg, and each of them was intramuscularly injected on days 1, 3, 7, and 14 with 1000 ng composition obtained from the preparation example 1 of the present invention. The experimental group B was the mice that underwent nerve truncation on their sciatic nerve of the left leg, and each of them was intramuscularly injected on days 1, 3, 7, and 14 with 5000 ng composition obtained from the preparation example 1 of the present invention. The level of muscle atrophy was observed to evaluate the effect of the composition of the present invention against muscle atrophy. The sciatic nerve of the right leg was not performed truncation in each group. The sciatic nerve truncation procedure was similar to that of Example 2, except that the sciatic nerve was directly truncated after being picked up.

Figure 14:
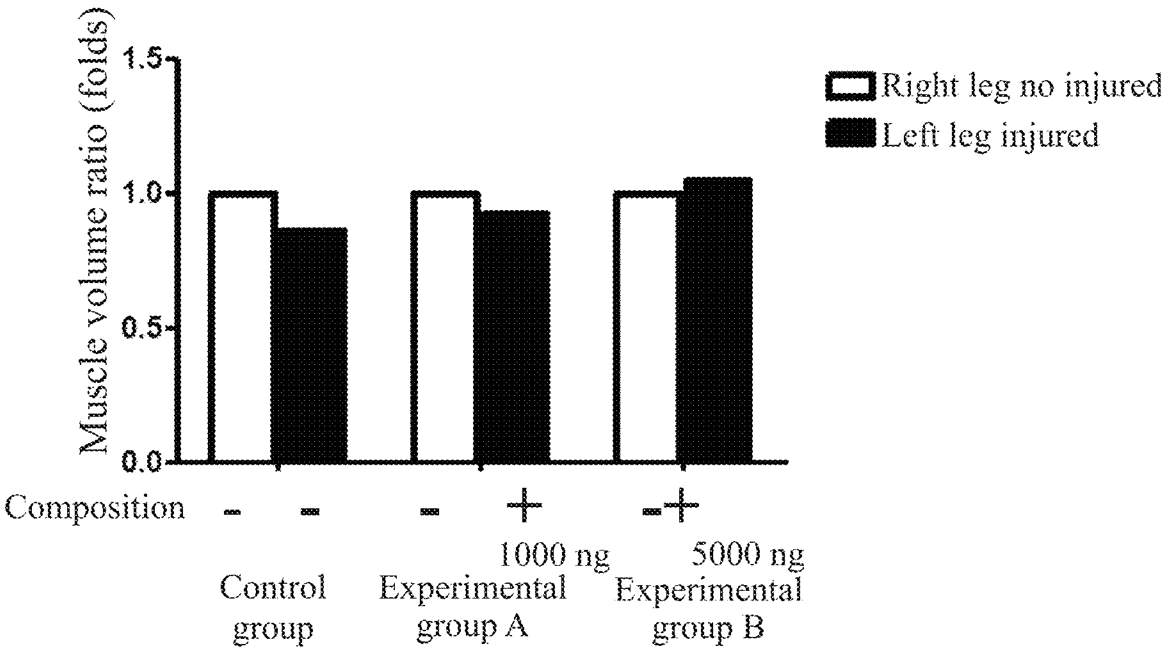
FIG. 14 is a bar graph related to the ratio of muscle volume after blocking sciatic nerve and then administered 1000 ng or 5000 ng composition of the present invention in experimental group A and experimental B of the present invention; wherein the sciatic nerve of the left leg was blocked, but the sciatic nerve of right leg was not blocked.

The results showed on day 28, the muscle volume of the left thigh of the control group was about 1375 $mm^3$ and the muscle volume of the right thigh was about 1560 $mm^3$. Since the right thigh was not subjected to sciatic nerve truncation surgery, the muscle volume of the right thigh was used as the reference ratio 1. The muscle volume ratio of the left thigh was the left thigh muscle volume divided by the right thigh muscle volume (as shown in the control group in FIG. 14), indicating that the left leg muscle of the control group was atrophied compared to the right leg muscle, and the right leg muscle was not atrophied. The muscle volume of the left thigh of the experimental group A was about 1289 $mm^3$, the muscle volume of the right thigh was about 1394 $mm^3$, because the right leg has not undergone sciatic nerve truncation surgery, so the muscle volume of the right thigh as a reference ratio 1. The volume ratio of the left thigh muscle was that the left thigh muscle volume divided by the right thigh muscle volume (as shown in experimental group A in FIG. 14). After sciatic nerve truncation surgery, the left leg muscle atrophy was significantly slowed down. The muscle volume of the left thigh of the experimental group B mouse was about 1958 $mm^3$, the muscle volume of the right thigh was about 1869 $mm^3$, because the right leg was not undergone sciatic nerve truncation surgery, so the muscle volume of the right thigh as a reference ratio 1. The volume ratio of the left thigh muscle was the muscle volume of the left thigh divided by the muscle volume of the right thigh (as shown in experimental group B in FIG. 14). Although the left thigh of the mice undergoes sciatic nerve truncation surgery, the level of muscle atrophy was not observed muscle atrophy due to the administration of the composition of the present invention.

Figure 15:
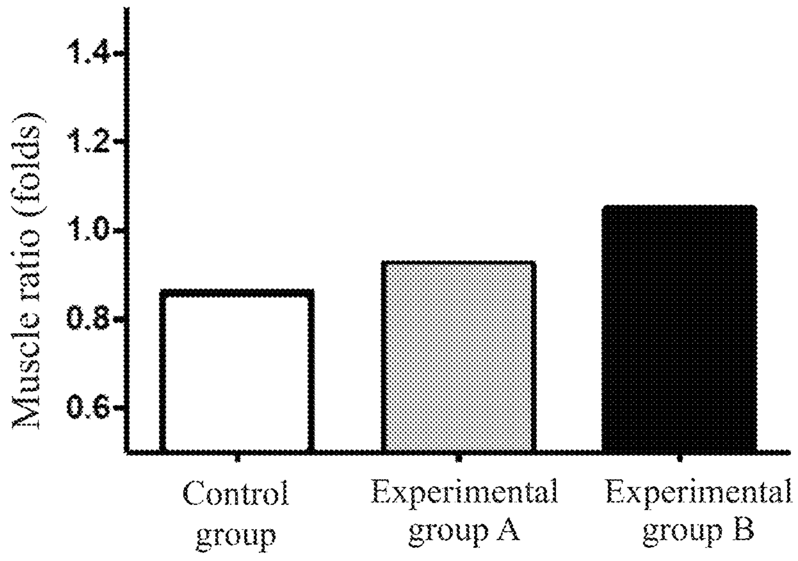
FIG. 15 is a bar graph related to the ratio of muscles obtained from the left leg muscle volume ratio divided by the right leg muscle volume ratio in the experimental group A and experimental B of FIG. 14.

As shown in FIG. 15, the muscle volume ratio of the left thigh/right thigh of the control group was about 0.87, showing atrophic state (less than 1 means that the atrophy state); the muscle volume ratio of the left thigh/right thigh of the experimental group A was about 0.92 experimental group, it showed a slowing of muscle atrophy compared with the control group. The muscle volume ratio of the left thigh/right thigh of the experimental group B was about 1.04, and showed the experimental group B could even maintain muscle volume compared with the control group. Thus, in addition the local muscle atrophy can be reduced or relieved in Example 2, the muscle volume can maintain the original state by administering the composition of the present invention in the case of the sciatic nerve truncation of the Example 3.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A composition for promoting local muscle growth or slowing local muscle atrophy, wherein the composition comprises a first polypeptide; a second polypeptide; and a linker between the first peptide and the second peptide, wherein the sequence of the first polypeptide, the linkerand the second polypeptide issetforth in SEQ ID NO: 17.

2. A method for promoting local muscle growth or slowing local muscle atrophy comprising a step of administeringto a subject in a local muscle in need thereof the effective amount of the composition as claimed in claim 1.

3. The method according to claim 2, wherein the composition is used for muscle atrophy caused by nerve trauma.

* * * * *